(12) United States Patent
Stark et al.

(10) Patent No.: US 9,211,551 B2
(45) Date of Patent: Dec. 15, 2015

(54) ELECTROSTATIC SPRAYING DEVICE AND A METHOD OF ELECTROSTATIC SPRAYING

(75) Inventors: John P. W. Stark, London (GB); Matthew S. Alexander, London (GB); Mark D. Paine, London (GB); Kate L. Smith, London (GB)

(73) Assignee: Queen Mary & Westfield College, London (GB)

(*) Notice: Subject to any disclaimer, the term of this patent is extended or adjusted under 35 U.S.C. 154(b) by 1273 days.

(21) Appl. No.: 12/600,625

(22) PCT Filed: May 19, 2008

(86) PCT No.: PCT/GB2008/001708
§ 371 (c)(1),
(2), (4) Date: Nov. 17, 2009

(87) PCT Pub. No.: WO2008/142393
PCT Pub. Date: Nov. 27, 2008

(65) Prior Publication Data
US 2010/0155496 A1    Jun. 24, 2010

(30) Foreign Application Priority Data

May 17, 2007 (GB) .................................. 0709517.7
Jun. 6, 2007 (GB) .................................. 0710879.8

(51) Int. Cl.
*A01G 23/10*  (2006.01)
*B05B 5/025*  (2006.01)
(Continued)

(52) U.S. Cl.
CPC ............. *B05B 5/0255* (2013.01); *B05B 5/047* (2013.01); *B05B 5/053* (2013.01); *H01J 49/165* (2013.01);
(Continued)

(58) Field of Classification Search
CPC .. B05B 5/0533; B05B 5/0255; B05B 5/1691; B05B 5/025
USPC ................. 239/690, 690.1; 250/281, 282, 288
See application file for complete search history.

(56) References Cited

U.S. PATENT DOCUMENTS 5,015,845 A    5/1991    Allen et al.
5,115,131 A    5/1992    Jorgenson et al.
(Continued)

FOREIGN PATENT DOCUMENTS

DE    19806253 A1    8/1999
EP    0468735 A1    7/1991
(Continued)

OTHER PUBLICATIONS

Paine, M. D., et al., "Controlled Electrospray Pulsation for Deposition of Femtoliter Fluid Droplets onto Surfaces," Journal of Aerosol Science, vol. 38, Mar. 3, 2007, pp. 315-324.
(Continued)

*Primary Examiner* — Arthur O Hall
*Assistant Examiner* — Viet Le
(74) *Attorney, Agent, or Firm* — Haynes and Boone, LLP

(57) ABSTRACT

An electrostatic spraying device (1) and method for dispensing a controlled volume of liquid in pulses using an emitter (2) having a spray area (29) from which the liquid can be sprayed, a means for injecting charges into the liquid, whereby, in use, the liquid (3) is delivered to the spray area by electrostatic forces and electrostatic spraying occurs in one or more pulses whilst the charges are injected. The charges may be injected by a time-varying or constant non-zero electric field so that electrospray occurs above a threshold value.

14 Claims, 25 Drawing Sheets

(51) Int. Cl.
B05B 5/047 (2006.01)
B05B 5/053 (2006.01)
H01J 49/16 (2006.01)
H05K 3/12 (2006.01)
G01N 30/72 (2006.01)
G01N 30/84 (2006.01)

(52) U.S. Cl.
CPC .......... *H05K 3/1241* (2013.01); *G01N 30/7266* (2013.01); *G01N 2030/8488* (2013.01); *H05K 2203/075* (2013.01); *H05K 2203/105* (2013.01)

(56) References Cited

U.S. PATENT DOCUMENTS

| | | | |
|---|---|---|---|
| 5,344,676 | A | 9/1994 | Kim et al. |
| 6,407,382 | B1 | 6/2002 | Spangler |
| 6,860,434 | B2 * | 3/2005 | Ahn et al. ............... 239/102.1 |
| 7,232,992 | B2 | 6/2007 | Whitehouse et al. |
| 8,840,037 | B2 | 9/2014 | Stark et al. |
| 2001/0032897 | A1 | 10/2001 | Iwata et al. |
| 2006/0262163 | A1 | 11/2006 | Nishio et al. |
| 2007/0084999 | A1 | 4/2007 | Miller et al. |
| 2007/0101934 | A1 | 5/2007 | Nishio et al. |
| 2009/0152371 | A1 | 6/2009 | Stark |

FOREIGN PATENT DOCUMENTS

| | | |
|---|---|---|
| EP | 0 468 735 A1 | 1/1992 |
| EP | 1 205 252 | 5/2002 |
| EP | 1 595 845 A1 | 11/2005 |
| EP | 1 788 375 | 5/2007 |
| EP | 1832349 A | 9/2007 |
| EP | 1 963 024 B1 | 4/2010 |
| EP | 2 162 228 B1 | 3/2012 |
| JP | 1998-000808 A | 1/1998 |
| JP | H10166593 A | 6/1998 |
| JP | H10181025 A | 7/1998 |
| JP | 2005-058810 A | 3/2005 |
| KR | 20000058944 A | 10/2000 |
| WO | 94/12285 A2 | 6/1994 |
| WO | WO 94/12285 | 6/1994 |
| WO | WO 94/12285 A | 6/1994 |
| WO | 98/56894 A1 | 12/1998 |
| WO | 98/58745 A1 | 12/1998 |
| WO | 01/71311 A2 | 9/2001 |
| WO | WO 01/71311 | 9/2001 |
| WO | 02/085538 A2 | 10/2002 |
| WO | 02/095362 A2 | 11/2002 |
| WO | 03/000431 A1 | 1/2003 |
| WO | WO 2005/014179 A1 | 1/2005 |
| WO | WO 2005/014179 A1 | 2/2005 |
| WO | WO 2007/030317 | 3/2007 |
| WO | WO 2007/066122 | 6/2007 |

OTHER PUBLICATIONS

M.D. Paine, M.S. Alexander, K. L. Smith, M. Wang, J.P.W. Stark: "Controlled electrospray pulsation for deposition of femtoliter fluid droplets onto surfaces" Journal of Aerosol Science, vol. 38, Mar. 3, 2007, pp. 315-324.
Examination Report dated May 26, 2010 in EP Application No. 08 750 639.0, 7 pages.
PCT Written Opinion of the International Searching Authority in Int'l App No. PCT/GB2008/001708, 16 pages.
GB Search Report in GB Application No. GB0709517.7, dated Jul. 25, 2007, 4 pages.
GB Search Report in GB Application No. GB0710879.8, dated Aug. 28, 2007, 4 pages.
Office action (Notice of Reasons for Rejection) dated May 31, 2012 in Japanese patent application No. 2008-543902 (2 pages), with translation (4 pages).
Notice of Allowance dated May 25, 2010 in Japanese patent application No. 2008-543902 (2 pages).
Office action (Non-Final Rejection) dated Dec. 7, 2012 in KR patent application No. 10-2008-7016524 (7 pages), with translation (7 pages).
English language Abstract of KR 20000058944 from Espacenet (1 page), Last updated May 12, 2011.
Notice of Allowance dated Jul. 3, 2013 in KR patent application No. 10-2008-7016524 with translation (3 pages).
PCT International Search Report of the International Searching Authority in Int'l App No. PCT/GB2008/001708, 5 pages, Oct. 23, 2008.
PCT International Preliminary Report on Patentability of the International Searching Authority in Int'l App No. PCT/GB2008/001708, 17 pages, Nov. 17, 2009.
Restriction Requirement dated Aug. 6, 2010 for U.S. Appl. No. 12/096,253, 7 pages.
Non-Final Office Action dated Nov. 30, 2010 for U.S. Appl. No. 12/096,253, 11 pages.
Final Office Action dated May 25, 2011 for U.S. Appl. No. 12/096,253, 13 pages.
Advisory Action dated Sep. 9, 2011 for U.S. Appl. No. 12/096,253, 3 pages.
Non-Final Office Action dated Jul. 3, 2013 for U.S. Appl. No. 12/096,253, 6 pages.
PCT International Search Report and Written Opinion of the International Searching Authority in Int'l App No. PCT/GB2006/004586, 10 pages, Feb. 9, 2007.
GB Search Report dated Mar. 8, 2006 for Application No. GB0524979.2, 1 page.
Chinese First Office Action mailed Apr. 27, 2010, in counterpart Chinese Patent Application No. 200680050762.6, 6 pages.
Chinese Second Office Action mailed Mar. 15, 2011, in counterpart Chinese Patent Application No. 200680050762.6, 9 pages.
Chinese Third Office Action mailed Nov. 23, 2011, in counterpart Chinese Patent Application No. 200680050762.6, 8 pages.
European Examination Report mailed Apr. 21, 2009, in related European Application No. 06 820 456.9, 3 pages.
European Examination Report mailed Dec. 2, 2008, in related European Application No. 06 820 456.9, 9 pages.
English translation of Japanese Office action (Notice of Reasons for Rejection) dated Mar. 5, 2013 in Japanese patent application No. 2010-507984, 4 pages.
English translation of Chinese Office action (Notification of the First Office Action) dated Aug. 1, 2012 in Chinese patent application No. 200880016463.X, 11 pages.
English translation of Chinese Office action (Notification of the Second Office Action) dated Jul. 3, 2013 in Chinese patent application No. 200880016463.X, 6 pages.
European Office action (Summons to attend oral proceedings) dated Apr. 8, 2011 in European patent application No. 08 750 639.0-2425, 5 pages.
English translation of Japanese Final Office action (Notice of Reasons for Final Rejection) dated Dec. 17, 2013 in Japanese patent application No. 2010-507984, 2 pages.
Japanese Final Office action (Notice of Reasons for Final Rejection) dated Dec. 17, 2013 in Japanese patent application No. 2010-507984, 2 pages.
Cloupeau, M. And Prunet-Foch, B., Electrostatic spraying of liquids in cone-jet mode, *Journal of Electrostatics*, 22, 135-159, (1989).
J. Fernández de la Mora and I.G. Loscertales, *J. Fluid Mech.*, 260, 155-184, (1994).
Smith, D.P.H., IEEE Transactions on Industry Applications 22, 527-533, (1986).
A.M Ganan Calvo, J Davila & A Barrero J Aerosol Science 28, 249-275 (1997).
R Juraschek and F.W. Rollgen, *Int. J. Mass Spectrom.* 177, 1-15, (1998).
MS Alexander, Paine, MD & Stark, JPW, Analytical Chemistry, 78, 2658-2664 (2006).
First Examination Report in related Indian Patent Application No. 1131/MUMNP/2008, 2 pages.

* cited by examiner a) b)

Nozzle exit
diameter ~ 90μm
Voltage ~ 2.0kV

Drop Ø ~42μm

Drop V = 19.1pL

Acetate substrate
Frequency 267Hz

ELECTROSTATIC SPRAYING DEVICE AND A METHOD OF ELECTROSTATIC SPRAYING

The present invention relates to an electrostatic spraying apparatus and a method of electrostatic spraying.

In conventional electrostatic atomisation or electrospray techniques the surface of an electrolytic liquid, typically of conductivity greater than $10^{-8}$ S/m, is charged by an applied electric field, typically of the order around $10^6$ V/m. Spraying occurs when the electrostatic forces on the fluid surface overcomes the surface tension of the liquid. The most stable spraying regime is that of the cone-jet mode, in which the balance between electrostatic and surface tension forces creates a Taylor cone, from the apex of which a liquid jet is emitted. This stable cone-jet only occurs within a particular range of liquid flow rate and applied voltage. When the voltage and/or the flow rate are below that required for stable cone-jet then other spray regimes occur, including dripping, electrodripping and spindle mode.

A particular electrospray method commonly used in electrospray ionisation mass spectrometry, as described in Int. J. Mass Spectrom. Ion processes 1994, 136, 167-180, is known as nanoelectrospray. A characteristic of nanoelectrospray is that the flow rate can be dictated by the voltage applied and the tube geometry, in particular the exit diameter. This has the advantage that electrospray can be achieved without the use of pumps or valves to force the liquid from a reservoir to the exit. The ability to controllably eject or deposit small volumes of fluid using this method has been identified in J. Aerosol Sci. 2007, 38, 315-324 as a promising technique for patterning surfaces with a range of fluids In electrostatic spraying of insulating fluids, with conductivity less than $10^{-8}$ S/m, the intrinsic conductivity is not sufficient to produce a large enough surface charge under the applied voltage in a similar manner to that of conventional electrospray behaviour observed with fluids of higher conductivity as described above. However, it has been shown that if a particular electrode geometry, for example using a sharpened needle as the electrode immersed in the fluid, is used it is possible to inject charges into the insulating fluid to allow the liquid to undergo spraying and jetting as described in J. Appl. Phys., 1976, 47, 5, 1964-1969. In this way it is possible to develop sufficient surface charge to spray the dielectric liquids in similar modes to that observed in conventional electrospraying. The mechanism of charge injection is not limited to a high voltage power supply and includes but is not limited to triboelectrically generated charge and piezoelectric devices.

It is also known from J. Appl. Phys. 1998, 64, 4278-4284 that for insulating fluids when the voltage is lower than that required to produce a stable cone-jet type mode, the liquid meniscus may undergo oscillations between a quasi-stable cone-jet and a deformed drop. This results in a pulsed spray with the intermittent emission of fluid droplets from the liquid surface. The production of pulses required a constant fluid flow rate, provided by a pump or a pressurized fluid.

In other known electrostatic atomisation or electrospray techniques, electrospray occurs continuously whilst a voltage or charging current is applied to the liquid to be sprayed. Control of the volume of liquid that can be electrosprayed is therefore relatively limited, since any variation in the time for which the voltage or charging current is applied directly affects the volume of liquid sprayed.

The known methods of electrostatic spraying of insulating fluids have the disadvantage that in order to start and stop the spray, it is necessary to start and stop the pumping method. It is not possible to accurately control the starting and stopping of the pump. In such an apparatus, even if the electric field or charging current is switched off the pump will continue to deliver liquid to the tube exit or spray area, resulting in dripping. This means that fine control of the liquid spray is not possible.

According to a first aspect of the present invention provides an electrostatic spray apparatus for dispensing a controlled volume of substantially non-conductive liquid in pulses, the apparatus comprising an emitter having a spray area from which the liquid can be sprayed. A means for injecting charges into the liquid, whereby, in use, the liquid is delivered to the spray area by electrostatic forces and electrostatic spraying occurs in one or more pulses whilst the charges are injected, and the apparatus preferably does not include a mechanical pump or any other means for pressurising the liquid.

This has the advantage that the electrostatic spray apparatus provides reliable pulses of sprayed non-conductive liquid droplets which can be accurately started and stopped.

According to a second aspect of the present invention provides a method of electrostatic spraying comprising providing an emitter for receiving a substantially non-conductive liquid. The emitter having a spray area from which liquid can be sprayed, injecting charges into the liquid, whereby the liquid is delivered to the spray area by electrostatic forces preferably without use of a mechanical pump or means for pressurising the liquid, and wherein the electric field strength or charging current, liquid viscosity and electrode geometry and emitter geometry are selected causing electrostatic spraying to occur in pulses whilst the electric field or charging current is applied.

Either positive or negative charges may be injected into the liquid or fluid.

Optionally, the means for injecting charges into the liquid or fluid is a pointed conductor such as for instance a metal needle or pin, having a tapered or sharpened point. This aids charge injection especially for non-conductive fluids or liquids.

Optionally, the point may be fully immersed within the liquid. The point may also be located within the emitter. The point may therefore not protrude through an aperture of the emitter. The emitter may be a cavity or capillary having an aperture or opening. The point may also be located inside the cavity and so without extending through the aperture of the cavity, i.e. before the aperture. This improves the charge injection thereby improving the regular nature and reliability of the pulses or emitted drops and also may reduce the occurrence of a jet or drops breaking up into smaller and more irregular droplets. This may be of particular importance for non-conductive fluids or liquids.

According to a third aspect of the present invention there is provided an electrospray apparatus comprising: an emitter for receiving liquids, the emitter having a spray area from which liquid can be sprayed; means for applying to the liquid a time-varying electric field or charging current; wherein, when the strength of the time-varying electric field or charging current is greater than a threshold strength, electrospray occurs in pulses whilst the electric field or charging current is applied; and wherein whilst electrospray occurs liquid is drawn to the spray area by electrostatic forces; and wherein, in use, the time-varying electric field or charging current strength is non-zero.

This has the advantage that the electrostatic spray apparatus provides reliable pulses of sprayed liquid droplets forming an accurately controllable volume of sprayed liquid.

Preferably, the strength of the time-varying electric field or charging current can be varied such that one or more pulses of electrospray are emitted during a first time period, and one or more pulses of electrospray are emitted during a second time period; wherein the rate of emission of pulses in the first time period is different to the rate of emission of pulses in the second time period.

Preferably, the length of the first time period is substantially the same as the length of the second time period.

Preferably, there is provided means for varying the length of time the strength of the electric field or charging current is above the threshold strength.

Preferably, the strength of the electric field or charging current is substantially constant whilst above the threshold strength.

According to a fourth aspect of the present invention there is provided a method of electrospraying comprising: providing an emitter for receiving liquids, the emitter having a spray area from which liquid can be sprayed; providing liquid to the emitter; applying to the liquid a time-varying electric field or charging current; wherein the time-varying electric field or charging current strength causes electrospray to occur in pulses whilst the electric field or charging current is greater than a threshold strength; and wherein whilst electrospray occurs liquid is drawn to the spray area by electrostatic forces; and wherein, in use, the time-varying electric field or charging current strength is non-zero.

Optionally, the method may be used for the manufacture of conductive tracks.

Advantageously, the strength of the time-varying electric field or charging current varies such that one or more pulses of electrospray are emitted during a first time period, and one or more pulses of electrospray are emitted during a second time period; wherein the rate of emission of pulses in the first time period is different to the rate of emission of pulses in the second time period.

Optionally, the method comprises varying the strength of the electric field or charging current in a cycle of constant period, the duty cycle when the strength is greater than the threshold value being variable.

Embodiments of the present invention will now be described with reference to the figures, in which.

Figure 1:
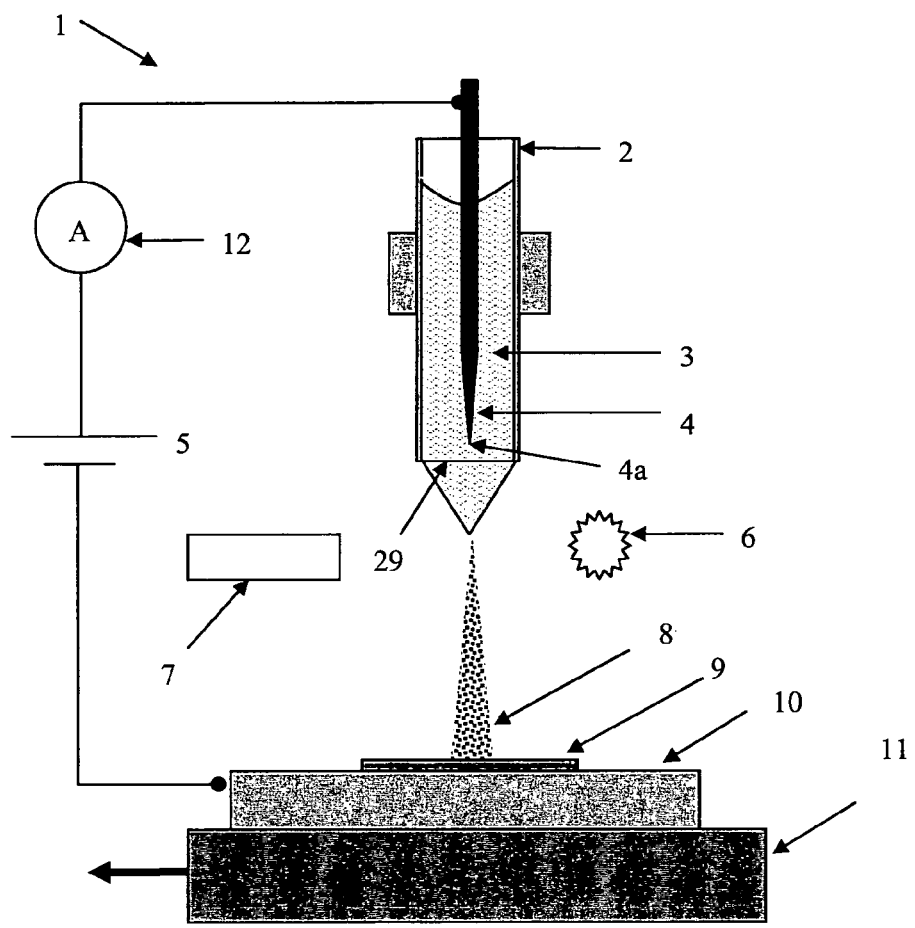
FIG. 1 is schematic side elevation view of the apparatus according to a first aspect of the present invention.

FIG. 1 shows an electrostatic spraying apparatus 1. An emitter tube 2 is capable of holding a liquid 3 to be electrosprayed. The tube 2 has a circular aperture or opening 29 from which the liquid 3 can be sprayed. The tube 2 acts as a liquid reservoir for the liquid 3. The liquid 3 is a low-conductivity or substantially non-conductive, i.e. substantially insulating, liquid. Alternatively, the liquid 3 may be a conductive liquid. However, the example provided below discusses the use of a substantially non-conductive liquid.

An emitter tube 2 is capable of holding a liquid 3 to be electrosprayed. The tube 2 has an aperture or opening 29 from which the liquid 3 can be sprayed. The aperture is preferably circular. The tube 2 acts as a liquid reservoir for the liquid 3. The liquid 3 is a low-conductivity or substantially non-conductive, i.e. substantially insulating liquid.

The substantially non-conductive liquid preferably has a conductivity of less than $10^{-8}$ S/m, and may have a conductivity less than $10^{-6}$ S/m. The liquid 3 may be a dielectric liquid. The terms substantially non-conductive and insulating should be taken to mean a liquid with low conductivity of less than $10^{-6}$ S/m, or optionally, less than $10^{-8}$ S/m.

An electrode in the form of a needle 4 is in contact with the liquid 3 to be sprayed. The needle 4 has a pointed end 4a tapered to a point. The pointed end 4a is adjacent to the opening 29 in the tube. The needle 4 is aligned with a longitudinal axis of the tube 2, and the pointed end 4a centred on the opening 29. The needle 4 is preferably made of metal. The pointed end 4a can emit positive or negative charges into the liquid 3 when a voltage is applied to the needle 4. The charges may be electrons (negatively charged) or made by capturing electrons (positively charged). The injection of charges into the liquid 3 can be considered to be a charging current.

A substrate electrode 10 is positioned at an appropriate distance from the opening 29 of the emitter tube 2, typically of the order 1 mm. The substrate electrode 10 is a solid square block of dimensions 2 cm×2 cm by 0.5 cm thickness, which is aligned with a longitudinal axis of the emitter tube 2. The substrate electrode 10 is grounded.

A high voltage power supply 5, capable of supplying a voltage of either polarity, is connected to the metal electrode 4. The high voltage power supply 5 can provide a constant voltage (i.e. DC) to the liquid. The voltage provided can be varied to a selected value.

A collector substrate 9 is placed on top of the substrate electrode 10. The collector substrate 9 receives the droplets of pulsed electrospray from the emitter tube 2.

A computerised high precision translation stage 11 supports the collector substrate 9 and substrate electrode 10, and can move the electrode 10 perpendicularly to the direction of spray.

The substrate surface may be coated with a pre-assembled monolayer of particles or molecules, and/or is coated with a pre-assembled sub-monolayer of particles or molecules. The substrate may be an insulator, a semiconductor, or a conductor. The substrate may in particular be silicon.

The emitter tube 2, substrate electrode 10 and collector substrate 9 may be housed in a grounded stainless steel vacuum chamber to allow the pressure of surrounding gas to be varied, and in particular, reduced.

The liquid 3 has a meniscus at the opening 29, the meniscus oscillating during electrospray. The meniscus may be in the form of a cone extending below the opening 29, as shown in FIG. 1. The oscillating liquid meniscus and the electrostatically produced droplets may be observed by a high speed charge coupled device (CCD) camera 7, illuminated by a cold light source 6.

The amount of charge injected into the fluid may be measured by a current monitoring device 12 connected to the emitter tube 2, in order to measure the current through the liquid.

The electrostatic spray apparatus 1 is an unforced system, meaning that there is no pump or valve connected between the aperture 29 and the liquid reservoir when the apparatus is in use. The liquid flow from the reservoir is induced only by electrostatic forces. The electrostatic forces are generated by the injected charges within the fluid and the electric field present both at the surface of the fluid and within the fluid itself due to the free charges.

The electrostatic spray apparatus 1 is configured to spray liquid 3 in discrete pulses, one or more pulses of liquid 3 being sprayed within a period in which voltage is applied to the needle 4. The pulses of spray occur automatically when the apparatus 1 is configured appropriately and are not directly generated by starting and stopping the applied voltage.

In order for pulsed spraying to occur, liquid viscosity, electrode and emitter geometry are selected so that the forces required to electrostatically pump the liquid at a flowrate close to the minimum stable spray flowrate are not too large. The electric field strength or charging current is also selected based on liquid viscosity, electrode and emitter geometry. The electric field strength is chosen such that electrostatic spraying occurs in pulses, without a constant corona discharge. For a specific emitter aperture diameter, or hydraulic resistance, for a large liquid viscosity the electric field strength or rate of injected charge may be higher. For a lower liquid viscosity, a lower charging current may be used. For a smaller emitter aperture diameter, or larger hydraulic resistance, then either the electric field strength or the amount of injected charge should be higher for a particular viscosity, or the viscosity should be lower for a particular field strength or injected charge current. These relationships are applicable to all of the described embodiments.

Many different liquids can be used in the electrostatic spray apparatus 1. Room temperature conductivities may range from a negligible conductivity up to $10^{-6}$ S/m. Low conductivity cryogenic liquids such as liquid nitrogen, liquid ammonia, liquid hydrogen or liquid oxygen may also be used. Viscosities from $1 \times 10^{-4}$ to 100 Pa·s may be used.

The electrostatic spraying apparatus 1 may be used as a printer, in order to spray an ink or print onto chips or substrates.

The electrostatic spray apparatus 1 has the particular advantages that the starting and stopping of the liquid pulses can be very accurately controlled. This is because liquid only flows from the capillary exit and emitted from the tube 1 when charge is injected into the fluid 3.

The charge can be injected into the low-conductivity or insulating fluid in a number of ways, including but not limited to injection from a sharp metal electrode at high voltage, from a piezoelectric charge injection device or a triboelectric charging mechanism. The starting and the stopping of the charge injection process can be very accurately controlled.

These different charging mechanisms may be used for any of the described embodiments.

The discrete pulses of ejected fluid are produced whilst a constant, i.e. non-pulsed, charging current or electric field is applied. The amount of liquid in each sprayed pulse is independent of the time for which the electric field or charging current is applied for. The constant electric field or charging current can be switched on and off to control when the discrete pulses should be emitted, and whilst the electric field or charging current is switched on the apparatus 1 emits a series of electrostatic spray pulses. The switching on and off of the electric field or charging current does not itself directly cause the pulses. The apparatus is configured such that when a constant electric field or charging current is applied it is in a mode which automatically generates pulses. The pulses of electrostatic spray are formed independently of any mechanical controlling means or electric field or charging current control means. This provides very consistent and uniform pulses, i.e. droplets, of electrostatically sprayed fluid.

The electrostatic spray apparatus 1 additionally has the advantage that each spray pulse occurs as a discrete jet, each jet containing a small and predictable volume of liquid. If there is relative movement between the tube and a surface being sprayed, then the surface will receive a series of discrete dots, which may be spaced from one another. The provision of series of dots may be advantageous for printing or other applications. This is preferably achieved by movement of the surface being sprayed, but may also be achieved by movement of the emitter.

The electrostatic spray apparatus may generate a pulsed electric field or charging current. Each pulse of electric field or charging current may contain one or more pulses of sprayed fluid. The electrostatic spray pulse will generally not start at the start of the electric field or charging current pulse, and will generally not finish when the electric field or charging current pulse finishes. The pulses of spray are independent of the pulse length of the applied electric field or charging current applied. The volume emitted by the electrostatic spray pulse or pulses will therefore depend on the number of electrostatic spray pulses occurring in the electric field or charging current pulse, and are not directly related to the length of the electric field or charging current pulse. This allows a tolerance in the length of the electric field or charging current pulse, without affecting the quantity of liquid emitted in the spray pulse.

For example, if it is wished to repeatedly spray a volume equal to one electrostatic spray pulse volume, the electric field or charging current can be applied in pulses to the needle 4. Whilst the electric field or charging current is applied, the electrostatic spray can occur in pulses at pre-determined frequency but will generally not start immediately, i.e. the device will not automatically spray as soon as the electric field or charging current is turned on. The on time for each pulse of electric field or charging current must be long enough to allow one spray pulse to be emitted but short enough to prevent two (or the required number) of electrostatic spray pulses being emitted. When the electric field or charging current is not applied, the electrode and/or substrate can be moved, in order to apply sequential spray pulses to a different location on the substrate. Any number of pulses of liquid can be sprayed before the electric field or charging current is reduced to inhibit further pulses. Increasing the charging current will increase the frequency of pulses, allowing further control of the deposition of the liquid.

The use of the apparatus will now be described with reference to FIG. 1. The same method also applies to the apparatus of FIGS. 1*b* and 18. An electric potential is applied to the liquid, such that the liquid is ejected from the tube 1 as a spray 8 in pulses. The spray 8 impacts on substrate 9. The translation stage 11 moves the collector substrate 9 and substrate electrode 10 perpendicularly to the direction of spray 8. The stage may remain stationery to allow one or a plurality of pulses of spray 8 to impact the substrate 9 at the same point.

This system 1 does not have a reservoir separate from the emitter tube. The tube 2 itself stores the liquid 3 to be sprayed. This embodiment allows the deposition of the liquid 3 onto the substrate 9 by the correct application of potential from the supply 5.

Alternatively, liquid may be stored in a reservoir in fluid connection with the emitter tube.

The distance between substrate 9 and emitter 2 can be varied to make the deposition area smaller or larger. Depending on the level of charge on the sprayed droplets, the sprayed droplets 8 may spread out as it travels away from the emitter 2, and so a larger distance between the substrate 9 and emitter 1 can provide a larger deposition area. The electrode 10 and/or collector substrate 9 are preferably placed on a translation stage 11, which may be computer controlled. The translation stage 11 provides relative movement between the electrode 10 and/or substrate 9 and the sprayed droplets 8 in order that the sprayed droplets 8 are deposited over a selected area of the substrate 9.

In an example apparatus with reference to FIG. 1, the emitter tube 2 is formed of uncoated borosilicate glass capillary with an outer diameter of 2 mm and inner diameter of 0.86 mm which tapers to an opening 29 of 42 μm diameter. The electrospray apparatus 1 was used with a fluid being a carbon loaded oil based ink with conductivity of approximately $10^{-12}$ S/m and viscosity of 10 mPa·s as the liquid 3 to be sprayed.

An appropriate distance between the end of the needle 4 and the opening 29 of the tube 2 was chosen, in this case a distance of 4 mm was used, and the distance between the tube opening 29 and the substrate material 9 was typically of the order 1 mm. The collector substrate 9 used was high quality photographic paper which was placed upon the steel substrate electrode 10 which was at ground potential.

In the absence of an applied voltage to the metal needle 4 or other means of charge injection no flow of liquid ink from the capillary occurred. As the voltage applied to the needle 4 (or other means) was increased from zero to a voltage of 900V droplets of ink were emitted from the capillary tube at a stable frequency in the low hundreds of Hertz range. As the voltage was increased above 900V the frequency of droplet emission and the liquid flow rate from the capillary exit increased. The frequency of droplets sprayed is constant at a constant voltage (i.e. constant rate of charge injection) when all other parameters of the apparatus are constant.

By moving the collector substrate 9 at a known constant velocity below the pulsing spray 8 using the computer controlled translation stage 11, the frequency of droplet emission could be determined by post-deposition imaging of the substrate.

Figure 2:
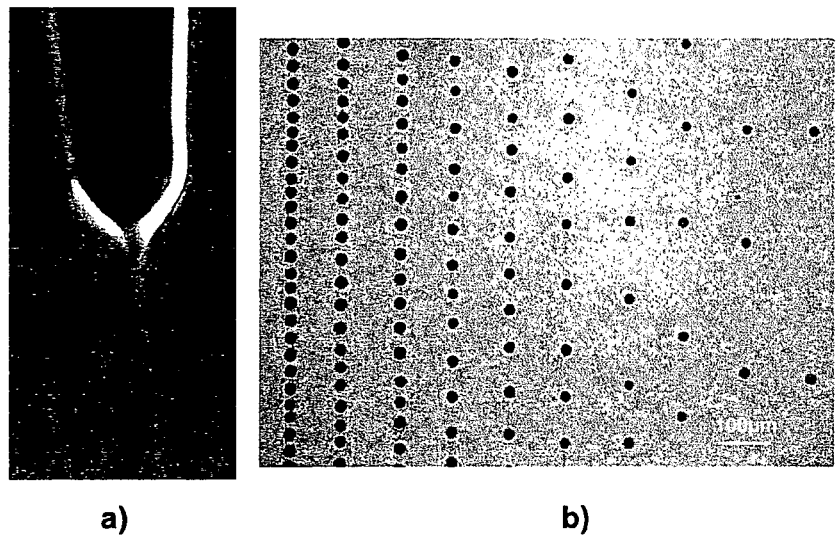
FIG. 2A is a side view of a pulled glass nozzle during electrostatic spraying of a liquid according to a first aspect of the present invention.
FIG. 2B is a plan view of a substrate after having received an electrostatic spray of a liquid according to the first aspect of the present invention.

An example image of the pulsing ink spray emanating from the capillary exit is shown in FIG. 2A. An example micrograph of the collector substrate 9 showing a series of lines of deposited dots of ink at differing emission frequencies is shown in FIG. 2B. The speed of movement of the substrate was selected to be 50 mm/s using the computer controlled translation stage 11. The frequency of emitted liquid pulses was varied by altering the applied voltage to the metal injector electrode 4.

Figure 3:
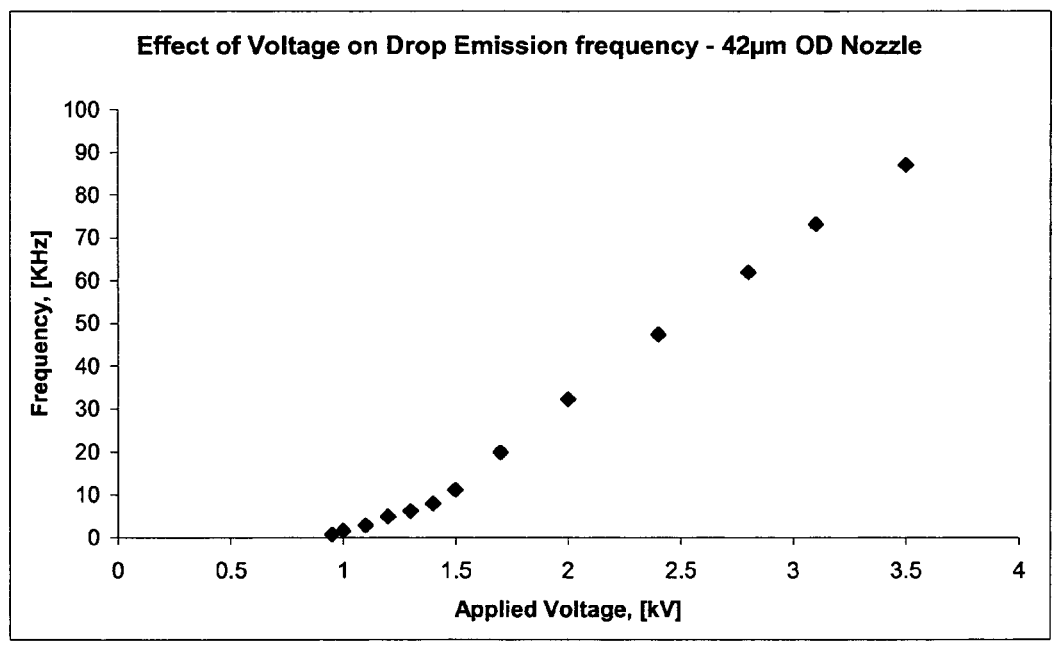
FIG. 3 shows a graph of the dependence of drop emission frequency on the applied voltage for a particular injector electrode and nozzle geometry using a first aspect of the present invention.

The droplet emission frequency was found to increase from approximately 300 Hz at 900V to around 80 kHz at an applied voltage of 4.0 kV as shown in the graph in FIG. 3. Over the range 900 to 4000V the frequency of spray pulses and droplet emission continued to increase and no stable cone-jet spraying regime was observed. At voltages above 4.0 kV an electrical discharge began to occur with periodic sparking.

Using known relationships between the remnant dot size produced on the photographic paper substrate and the original pulse volume deposited the liquid volumes emitted in each electrostatic spray pulse were calculated to be of the order 1-3 picoliters.

Figure 4:
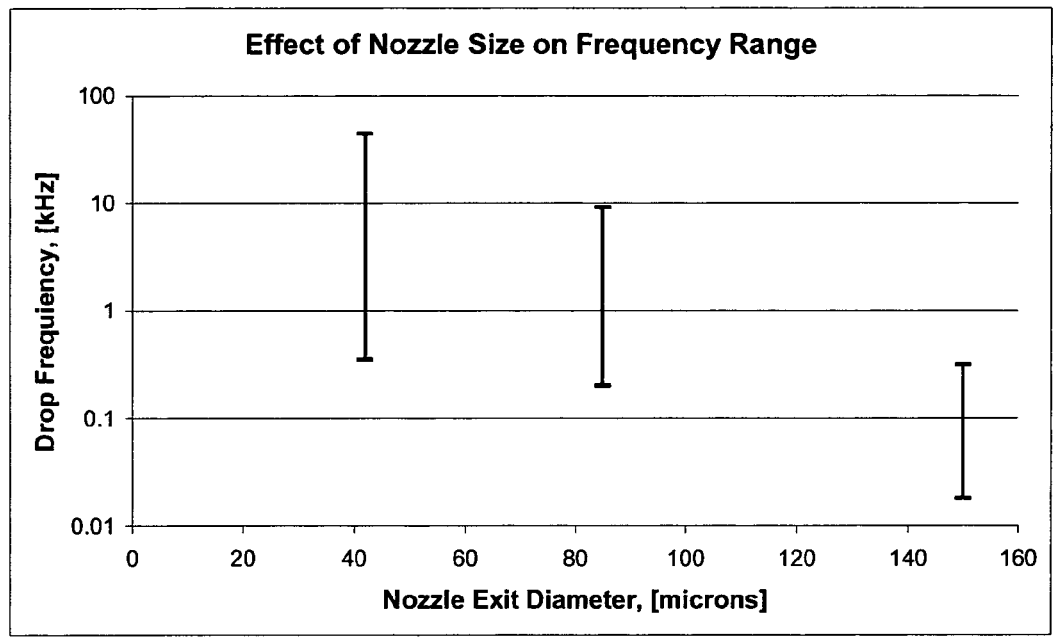
FIG. 4 shows a graph of drop emission frequency range achievable with different nozzle dimensions when spraying in accordance with the first aspect of the present invention.
Figure 5:
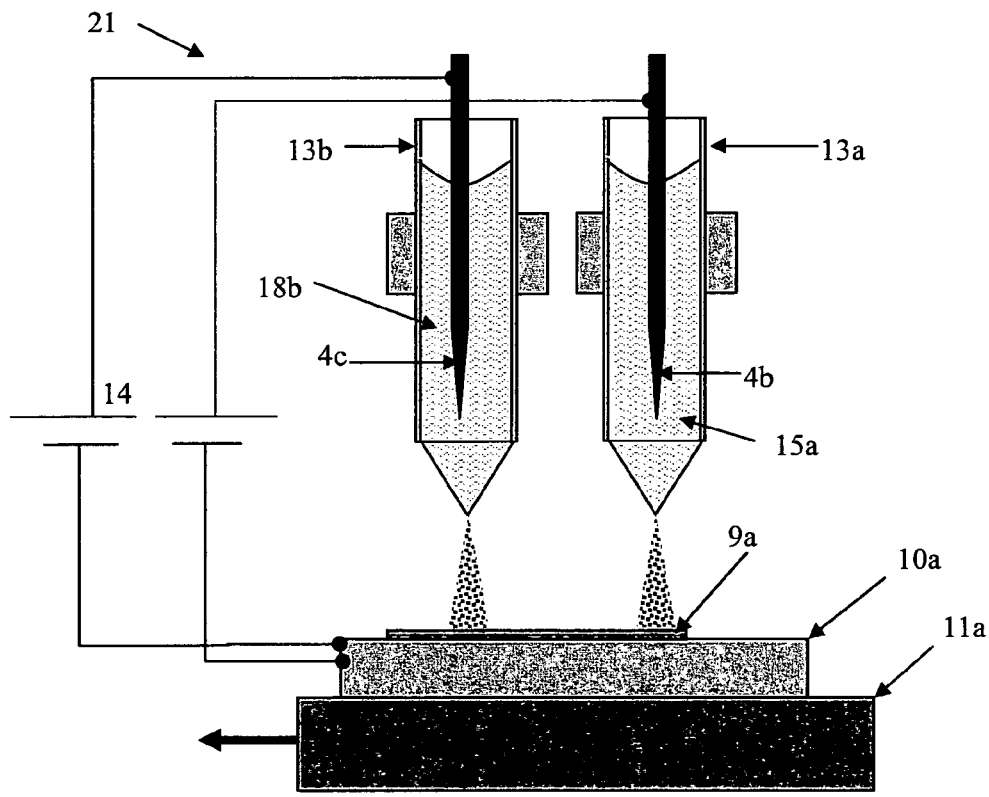
FIG. 5 is schematic side elevation view of an apparatus according to a second embodiment of the present invention.

FIG. 4 shows the effect of varying emitter/nozzle size on the range of drop emission frequencies achievable due to changes in the applied field. From the figure it is shown that the minimum and maximum drop emission frequencies are generally lower when a larger emitter/nozzle exit diameter is used. The liquid is the same carbon loaded oil based ink as described above, including data from spraying with larger nozzles than the 42 micron one previously discussed.

FIG. 5 shows a modification of the embodiment of the electrostatic spray apparatus of the present invention shown in FIG. 1. The electrospray apparatus 21 shown in FIG. 5 comprises two emitter tubes 13*a*, 13*b*, each tube 13*a*, 13*b* substantially the same as tube 2 described above. Alternatively, any number of emitters may be used. The first tube 13*a* contains a first liquid 15*a* to be sprayed. The second emitter tube 13*b* contains a second liquid 15*b* to be sprayed. A first pointed electrode 4*b* is located within the first emitter tube 13*a*, and aligned with the longitudinal axis of the tube 13*a*. A second pointed electrode 4*c* is located within the second tube 13*b*, and aligned with the longitudinal axis of the second emitter tube 13*b*. A power supply is connected to the first electrode 4*b*. The same power supply 14, or a different power supply, is connected to the second electrode 4*c*.

The electrospray apparatus 21 further comprises a substrate 9*a*, on to which the liquids 15*a*, 15*b* can be sprayed. The substrate 9*a* is mounted on a electrode 10*a*, which is at ground potential. The electrode 10*a* may be connected to the or each power supply. The substrate 9*a* and grounded electrode 10*a* may be mounted on a translation stage 11*a*, for moving the substrate 9*a* whilst at a constant distance from the emitter tubes 13*a*, 13*b*. Each of the emitter tubes 13*a*, 13*b* has an opening through which the liquid 15*a*, 15*b* can be sprayed. A second power supply 14 is connected between an electrode 10 and the immersed metal electrode 4B. The remaining features of FIG. 5 are as described for FIG. 1. When a potential is applied to the first and/or second metal electrode in contact with the fluid in the respective emitter tube 13a,13b, a pulsed electrostatic spray is produced from the respective tube 13a, 13b.

FIG. 5 shows two emitter tubes, however more than two tubes can be used together. The tubes may be arranged in a two-dimensional array.

Figure 6A:
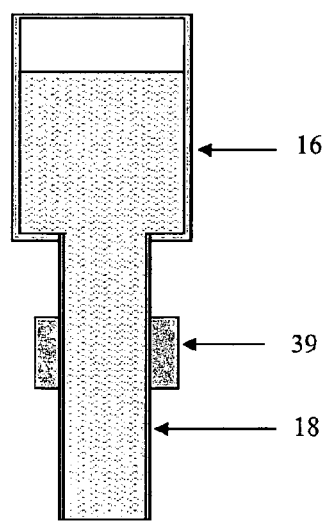
FIGS. 6A, 6B and 6C are schematic side elevation views of an apparatus according to a third embodiment of the present invention.
Figure 6B:
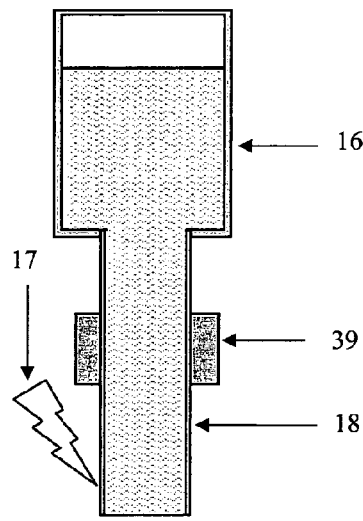
Figure 6C:
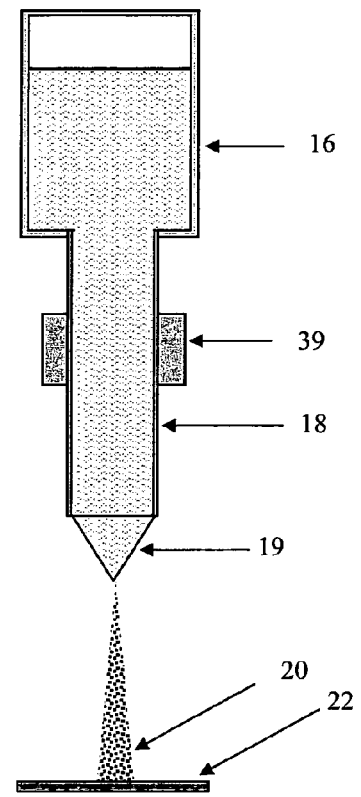

FIGS. 6A, 6B, 6C show a further embodiment of the electrostatic spray apparatus of the present invention. An emitter tube 18 is in the form of a capillary tube connected to an insulating fluid reservoir 16 which contains the liquid to be sprayed. A triboelectric charge 17 is transferred to the capillary tube 18 to initiate a spraying of the fluid. The duration of the fluid spray and nature of the sprayed pulses is dependent on the amount of injected charge.

Figure 7:
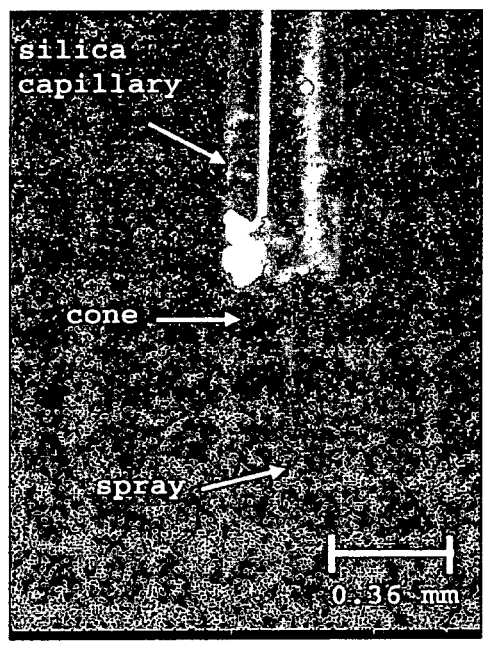
FIG. 7 is an image of an electrostatic spray of a liquid produced using the apparatus according to the third embodiment of the present invention.

The liquid to be sprayed was Dow Corning FS1265 silicone oil. An opening is provided in the capillary 18 through which electrospray can occur. In contrast to the embodiment of FIG. 1, no pointed electrode is present in the capillary 18. This entire system was held by an insulating support 39 below which was an optional insulating substrate 22. A section of rubber 17 was then used to transfer charge to the silica capillary 18 triboelectrically, as shown in FIG. 6B. Once the charge was transferred to the silica capillary a cone 19 and spray 20 emanated from the capillary as shown in FIG. 6C. The nature and duration of the spray depended on the amount of charge transferred to the capillary and would last anywhere between 5 and 30 seconds and exhibited both pulsation and continuous cone-jet mode spraying. An example of which is shown in FIG. 7 where a image of a cone-jet spray from of the silicone oil is shown at the tip of the silica capillary.

The frequency of droplets sprayed during or after application of a triboelectric charge may change as the charge is dissipated.

Figure 8:
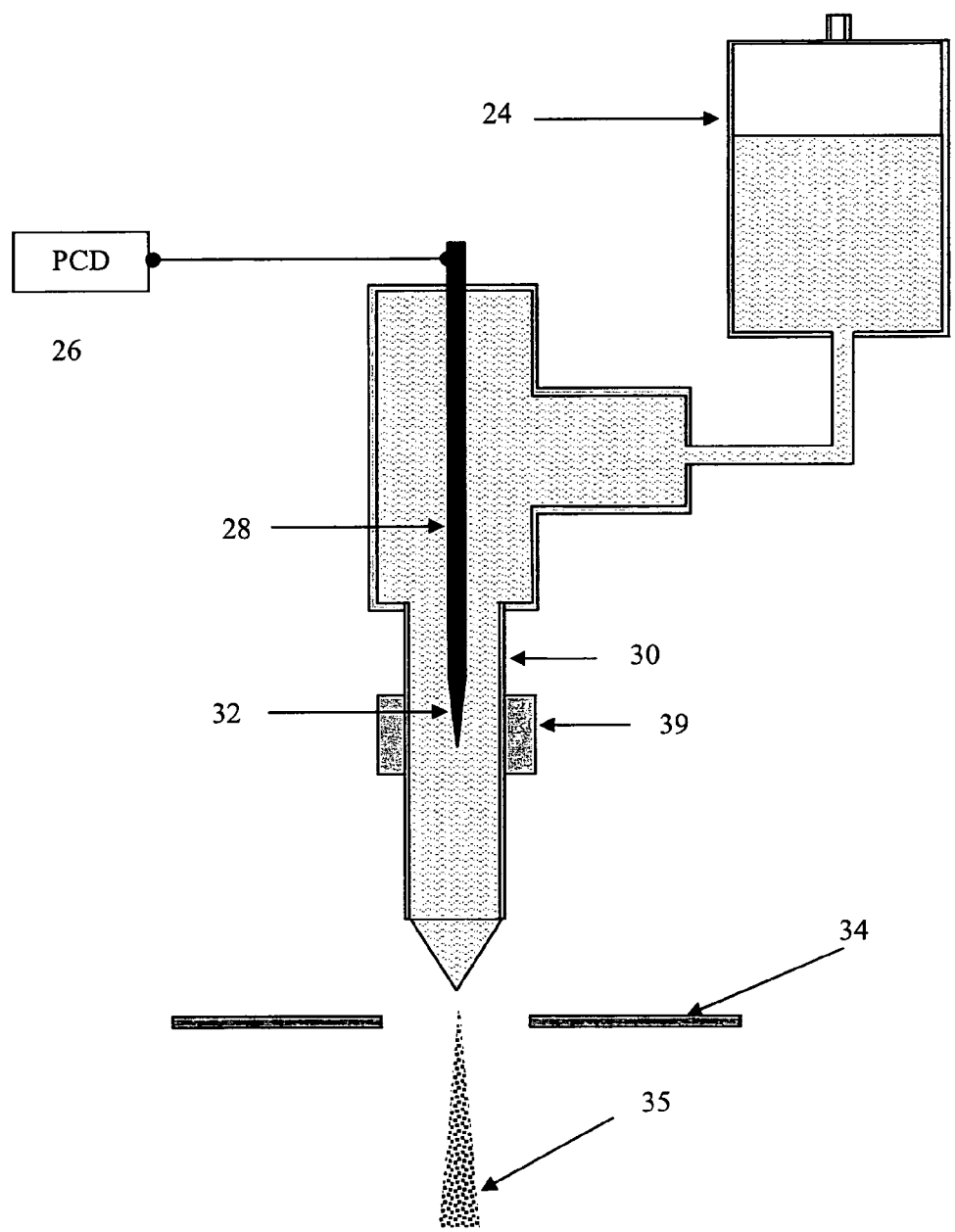
FIG. 8 is a schematic side elevation view of an apparatus according to a fourth embodiment of the present invention.

FIG. 8 shows a further embodiment of the electrostatic spray apparatus of the present invention wherein the emitter tube 30 is in the form of a capillary tube connected to a fluid reservoir 24 which contains the liquid to be sprayed. The charging current is delivered piezoelectrically by the piezoelectric charging device 26 to a metal injector electrode 28 which is at least partially immersed in the fluid to be sprayed. The field generated at the needle tip 32 due to the piezoelectrically generated charge causes the fluid to flow and exit the capillary tube 30 in the form of a pulsed spray of fluid. The counter electrode 34 may be a substrate to receive the fluid or may include an open aperture to allow the fluid exiting the capillary tube to be sprayed into the surrounding gaseous atmosphere or vacuum.

With reference to FIG. 8, the liquid to be sprayed is Dow Corning FS1265 silicone oil. The liquid was held in an insulated reservoir 24, which is preferably unpressurized. Connected to the reservoir 24 is an insulated emitter tube in the form of a silica capillary 30. The capillary is held by an insulating support.

An electrode 28 with a sharp pointed geometry section 32 extends into the capillary 30 and is at least partially immersed in the fluid to be sprayed. A piezoelectric charging device (PCD) 26 was electrically connected to the electrode 28. Upon activation of the piezoelectric device 26 charge was delivered to the fluid through the electrode 28 resulting in pulses of spray 35

This embodiment may comprise an electrode having an aperture 34, the spray 35 ejected through the aperture 34. When the charging current delivered to the fluid by the PCD 26 is sufficiently high, a stable cone-jet spray of fluid can be emitted from the capillary 30.

Alternatively, the arrangement shown in FIG. 8 may be used to deliver fluid to a substrate (not shown in FIG. 8) located on the other side of the aperture to the emitter tube 30. For instance, this arrangement may be used to deposit ink onto paper or other printable material without requiring an electrode on its underside, i.e. there is no requirement for the printable material to be placed between the emitter tube 30 and the electrode 34.

Figure 9:
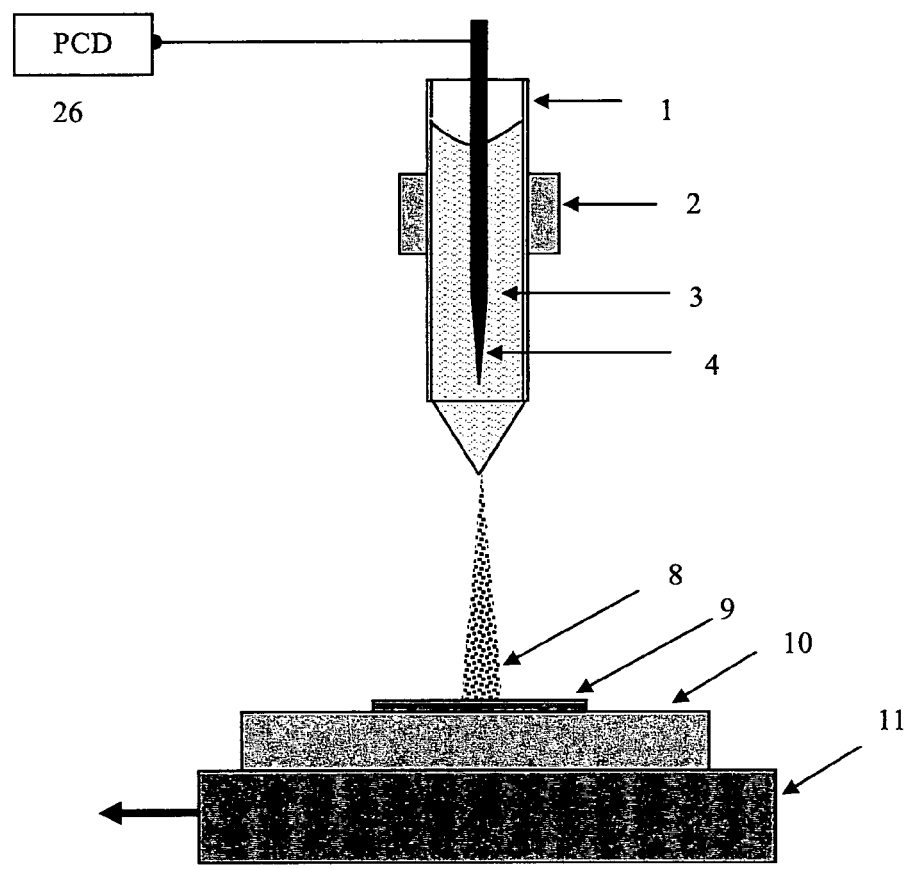
FIG. 9 is a schematic side elevation view of an apparatus according to a fifth embodiment of the present invention.

FIG. 9 shows a further embodiment of the invention, substantially as described with respect to FIG. 1. A PCD 26 as described for FIG. 8 is used to supply the charges.

Figure 10:
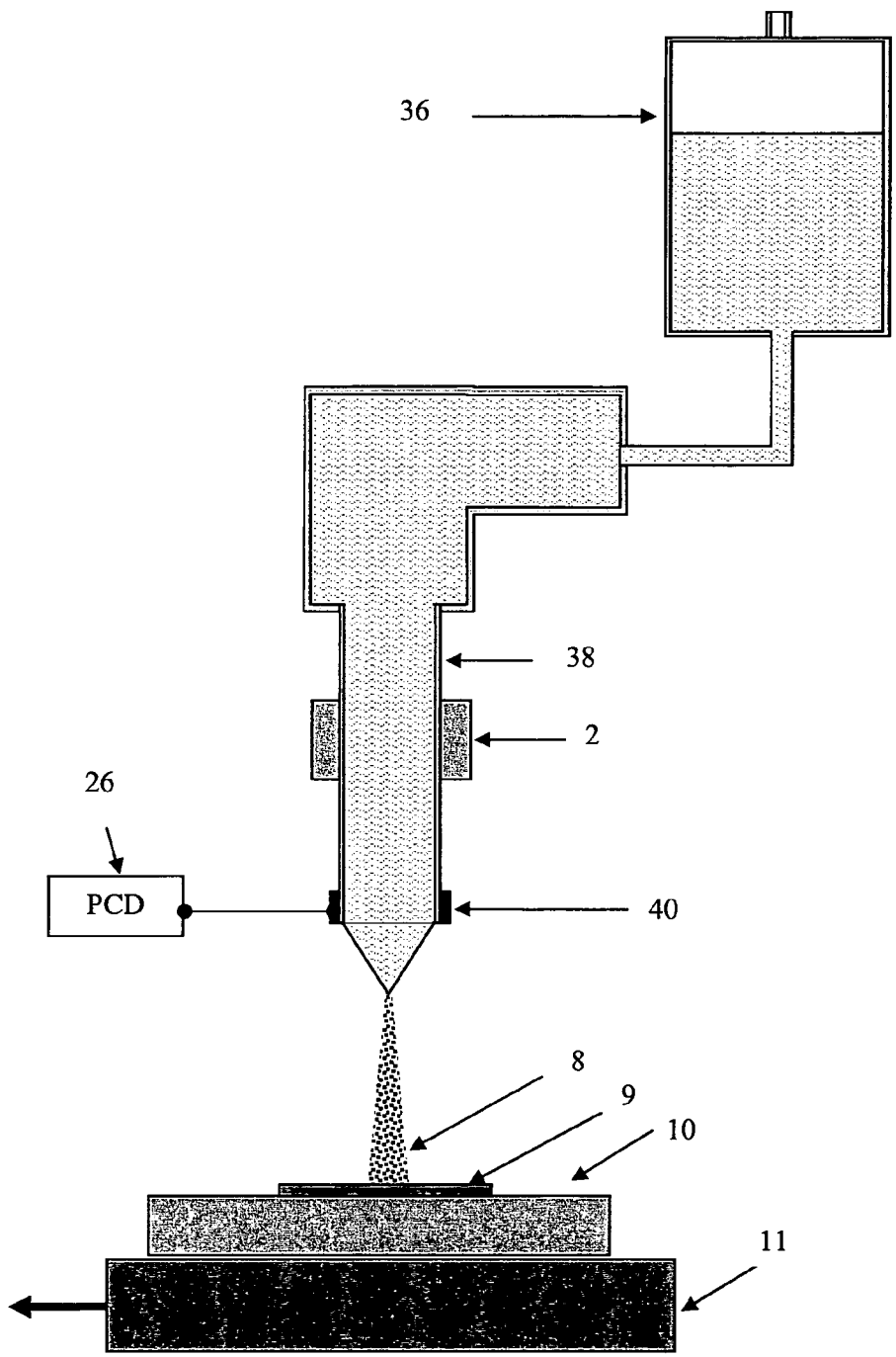
FIG. 10 is a schematic side elevation view of an apparatus according to a sixth embodiment of the present invention.

FIG. 10 shows a modification to the electrostatic spray apparatus of the present invention shown in FIG. 8 wherein the charge injection electrode is in the form of a metal coating 40 on the outer surface of the capillary tube 38 which contains the liquid to be sprayed. The charging current is delivered piezoelectrically by the piezoelectric charging device 26 to the metal injector electrode 40 which is at least partially in fluid communication in the liquid to be sprayed. The field generated due to the piezoelectrically injected charge causes the fluid to flow and exit the capillary tube 38 in the form of a charged liquid spray. The collector substrate 9 and substrate electrode 10 may be placed on a computer controlled translation stage 11 to allow relative movement between the collector surface and the liquid spray.

Figure 11:
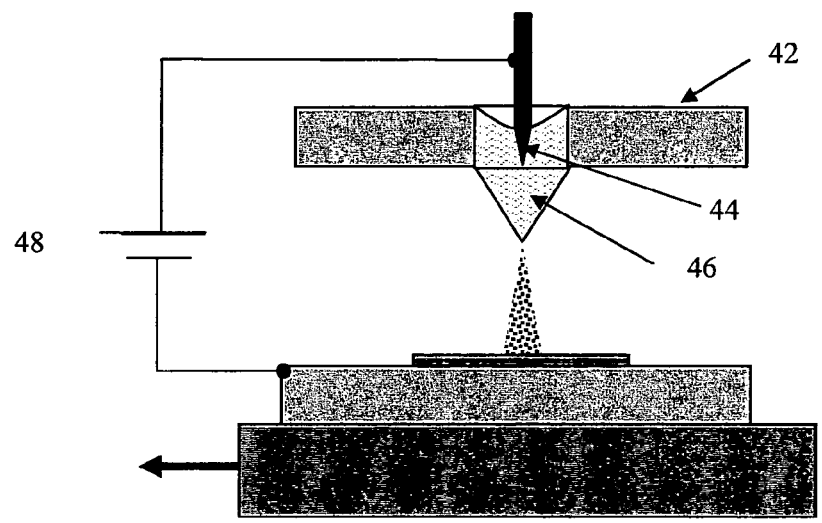
FIG. 11 is a schematic side elevation view of an apparatus according to a seventh embodiment of the present invention; is

FIG. 11 shows a modification of the embodiment of the electrostatic spray apparatus for the present invention shown in FIG. 1 or FIG. 5. In FIG. 11, the emitter is not in the form of a capillary tube, but is formed from any material 42 that can define a reservoir to store a liquid 46. An orifice is formed in the reservoir, from which the liquid may be sprayed. This embodiment may be microfabricated. A high voltage power supply 48 may be connected to the material 42 or a sharpened metal electrode 44 located in the reservoir in order to inject charge into the fluid 46. The embodiment of FIG. 11 functions in the same manner as FIGS. 1 and 5.

Any of the embodiments described above may have at least the emitter and substrate located in a vacuum chamber, from which air is substantially evacuated.

Figure 12:
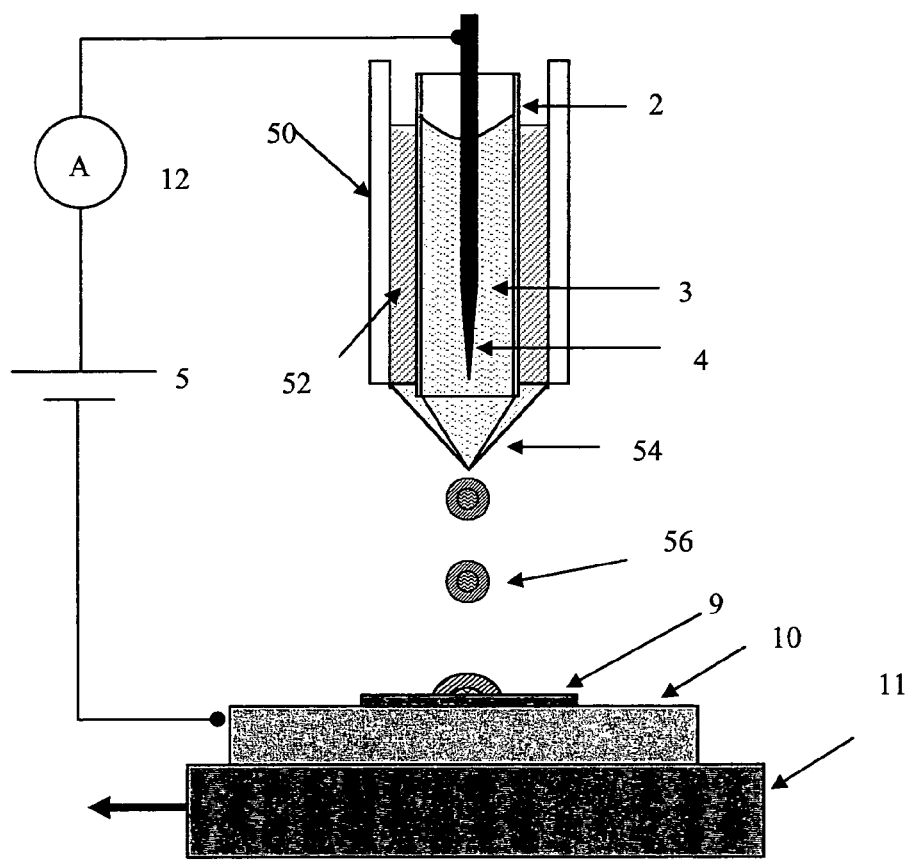
FIG. 12 is a schematic side elevation view of an apparatus according to an eighth embodiment of the present invention.

FIG. 12 shows a further embodiment of the electrospray apparatus of the present invention. The emitter tube 2, liquid 3, pointed electrode 4 and power supply 5 are substantially as shown in FIG. 1 or FIG. 5 or FIG. 11. The substrate 9, grounded electrode 10 and translation stage 11 are also as described above.

A tube 50 is arranged co-axially around the emitter tube 2, an opening of the emitter tube 50 surrounding the opening of emitter tube 2. The tube 50 contains a second fluid 54, such that the opening of tube 2 through which electrospray occurs from emitter tube 2 is located within the second fluid 54.

The second fluid 54 is different to the electrostatically sprayed liquid. The second fluid 54 may be either a liquid or a gas, and is contained within a container 52. The container 52 may be sealed or connected to a reservoir of fluid.

The second fluid 54 is preferably immiscible with the fluid to be electrostatically sprayed, but may be partially miscible with the fluid to be sprayed. The second fluid 54 may be static or flowing.

The second fluid 52 is preferably immiscible with the fluid to be electrostatically sprayed 3, but may be partially miscible with the fluid to be sprayed. The second fluid 52 may be static or flowing.

Spraying through the second fluid allows drops of the first fluid to be produced within a coating or film of the second fluid 56. This can allow the atomisation of encapsulated fluids into gaseous, liquid or vacuum environments or the deposition of encapsulated liquid drops onto the receiving substrate material 9.

Figure 13:
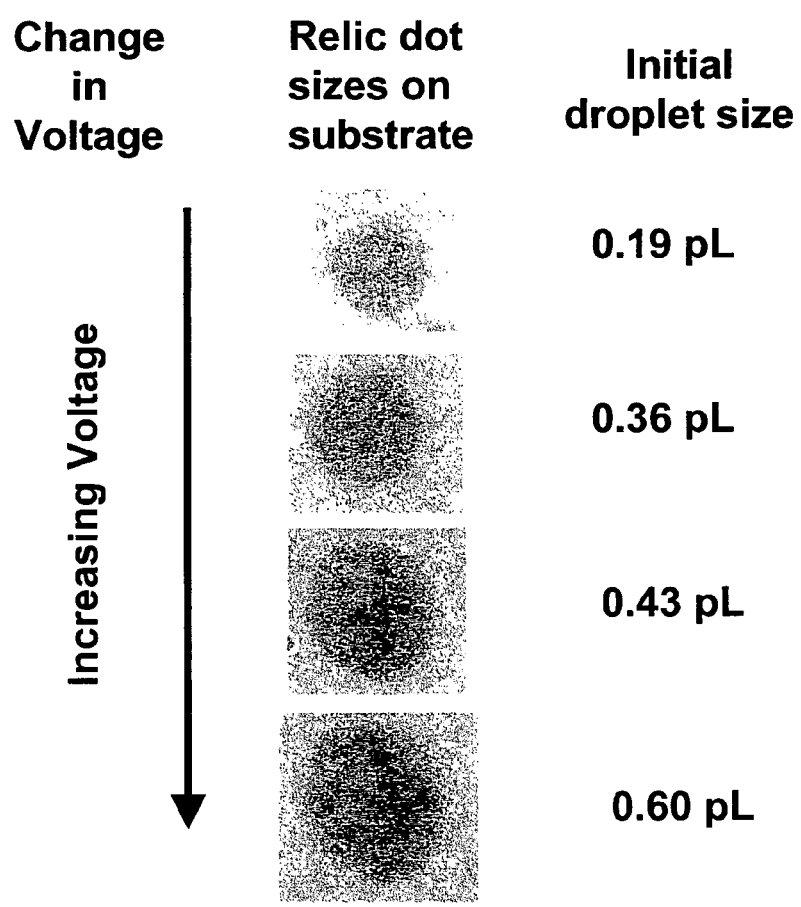
FIG. 13 shows a series of spray droplets illustrating the variation in emitted drop volume achievable by variation of the applied field or charging current from the same nozzle emitter geometry.

FIG. 13 illustrates the variation of emitted drop volume of a carbon loaded oil based ink due to changes in the applied field to the injector electrode in a similar arrangement to that shown in FIG. 1. On increasing the applied voltage to the metal needle both the frequency of droplet emission and the volume of each droplet were increased over the voltage range shown.

Figure 14:
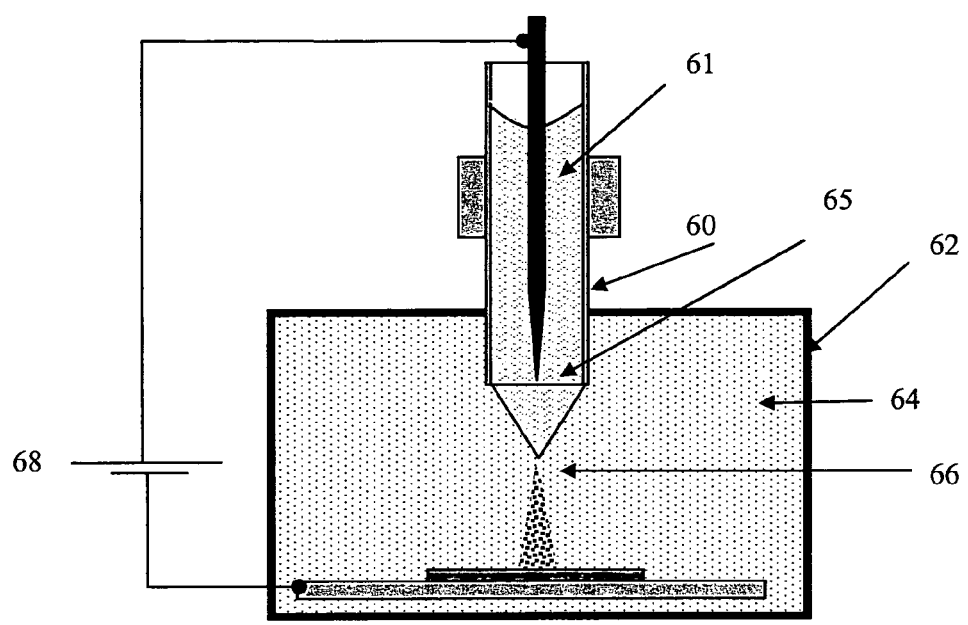
FIG. 14 is a schematic side elevation view of an apparatus according to a ninth embodiment of the present invention.

FIG. 14 shows a further embodiment of the invention. An emitter tube 60 contains a first liquid 61 to be electrosprayed. The tube 60 has a pointed electrode connected to a power supply 68, substantially as described for FIG. 1. The emitter tube 60 has an opening 65 through which the pulses of electrospray of liquid 61 are emitted. The opening 65 is located within a container 62. The container 62 contains a second fluid 64 different to the electrostatically sprayed liquid. The second fluid 64 may be either a liquid or a gas. The container 64 may be sealed or connected to a reservoir of fluid.

The second fluid 64 is preferably immiscible with the fluid to be electrostatically sprayed, but may be partially miscible with the fluid 61 to be sprayed. The second fluid 64 may be static or flowing.

A substrate and grounded electrode, and/or translation stage as previously described may also be located within the container 62.

Spraying through the second fluid allows drops of the electrostatically sprayed liquid to be dispersed controllably in the second fluid. This allows the formation of an emulsion, for example an oil/water emulsion or a nano-emulsion. It may also provide for the formation of particles having the electrostatically sprayed liquid contained within a solidified shell of the second liquid. Additionally, a volatile liquid may be sprayed in an involatile second liquid.

All of the described embodiments are configured to produce pulses of electrospray whilst charges are injected into the substantially non-conductive or conductive liquid or fluid to be electrosprayed. The pulses are not directly caused by the starting and stopping of the injection of charges, but are inherent in the configured system.

FIG. 1B shows a further embodiment of the electrospray apparatus of the present invention. This apparatus is configured to spray a conductive liquid.

A capillary emitter tube 70 contains liquid 74 to be sprayed. A high voltage power supply 79 is connected between an extractor electrode 78 and the emitter tube 70. An electric potential may be applied to the conductive surface of the emitter 70 by a conducting fitting 72. The high voltage power supply 79 provides a potential difference between the electrode 78 and the emitter 70.

The extractor electrode 78 is held at an appropriate distance from the emitter tip. On a side surface of the electrode 78 facing the emitter tube 70 a target substrate 77 can be placed.

The substrate may be coated with a pre-assembled monolayer of particles or molecules, and/or is coated with a preassembled sub-monolayer of particles or molecules. The substrate may be an insulator, a semiconductor, or a conductor.

In use, an electric potential is generated by the supply 79, such that liquid is ejected from the tube 70 as a jet or spray 76 in pulses. The spray 76 impacts on substrate 77. A computerised high precision translation stage 80 supports the substrate 77 and electrode 78, and can move the electrode 78 perpendicularly to the direction of the spray 76.

FIG. 18 shows an example of a different embodiment of the electrospray apparatus for the present invention than shown in FIGS. 1 and 1*b*. In FIG. 18, an emitter is not in the form of a capillary tube, but is formed from any material 85 that can define a reservoir to store a liquid 86. An orifice is formed in the reservoir, from which the liquid may be electrosprayed. This embodiment may be microfabricated.

A layer of material 87 is sandwiched between the material 85 and a layer 89. The layers of material 87, 89 define a recess around the orifice. The materials 85, 89 are preferably electrically conductive, or have electrically conductive elements embedded. The material 87 is preferably non-electrically conductive.

A high voltage power supply 79 is connected to the material 85, and is preferably also connected to the material 89. The high voltage power supply 79 is configured such that an electric field is generated in the liquid 86, to cause pulses of electrospray as described above. This illustrates an example of an integrated electrode.

In order for pulsed spraying to occur using either the apparatus of FIG. 1, 1*b* or 18, liquid viscosity, electrode and emitter geometry are selected so that the forces required to electrostatically pump the liquid at a flowrate close to the minimum stable spray flowrate are not too large. The electric field strength or charging current is also selected based on liquid viscosity, electrode and emitter geometry. The electric field strength is chosen such that electrostatic spraying occurs in pulses, without a constant corona discharge. For a specific emitter aperture diameter, or hydraulic resistance, for a large liquid viscosity the electric field strength or rate of injected charge may be higher. For a lower liquid viscosity, a lower charging current may be used. For a smaller emitter aperture diameter, or larger hydraulic resistance, then either the electric field strength or the amount of injected charge should be higher for a particular viscosity, or the viscosity should be lower for a particular field strength or injected charge current. These relationships are applicable to all of the described embodiments, in particular to the electrospraying of both conductive and non-conductive liquids.

The volume of liquid in each drop has been found to increase as the charging current or electric field is increased over part of the range of voltages at which pulses of electrospray occurs. For example, increasing drop volume with increasing voltage has been found to occur between 900 V and 3000 V applied. Increasing the charging current or electric field thus increases both the frequency of emitted droplets and the volume of liquid in each droplet.

The above description applies to both the electrospraying of conductive and non-conductive liquids using apparatus based on either FIG. 1, 1*b* or 18. Apparatus based on FIG. 1, 1*b* or 18 may have a plurality of emitters, which may be arranged in an array. A separate reservoir may be provided, in fluid connection with the emitter.

The emitter may not be in the form of a capillary tube, but may be formed from any material that can define a reservoir to store a liquid. An orifice is formed in the reservoir, from which the liquid may be sprayed. This embodiment may be microfabricated. A high voltage power supply or other means for charge injection may be connected to the material or a sharpened metal electrode located in the reservoir in order to inject charge into the fluid.

The emitted drop volume of a liquid varies due to changes in the applied field to the injector electrode. On increasing the applied voltage or charging current to the metal needle or other means for change injection both the frequency of droplet emission and the volume of each droplet were increased, over part of the range at which electrospray occurs. The volume of each drop may reach a peak, and then decrease. The drop volume relationship to applied voltage may be dependent on the properties of the liquid and emitter geometry.

Figure 1B:
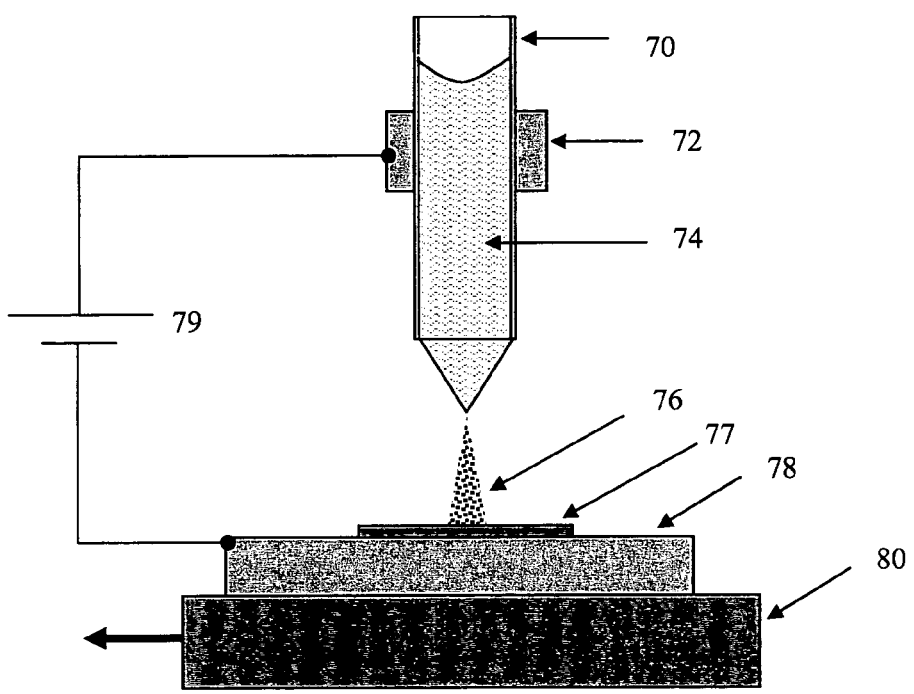
FIG. 1b is a schematic side elevation view of a tenth embodiment according to the present invention, given by way of example only.
Figure 18:
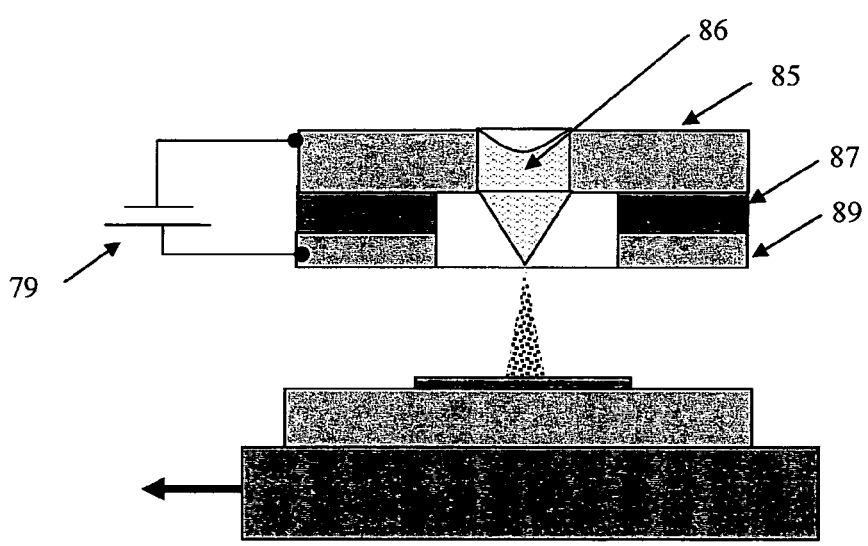
FIG. 18 shows an eleventh embodiment of the present invention having an integrated electrode

The electrospray pulses can be accurately controlled using the apparatus of FIG. 1, FIG. 1b or 18. It may be required to deposit one drop, or a pre-determined number of drops, at the same point in the substrate. It is therefore necessary to control the volume of liquid which is electrosprayed before ceasing electrospray to allow movement of the translation stage. Alternatively, it may be required to control the rate at which electrospray occurs onto a moving or stationery translation stage.

Figure 7A:
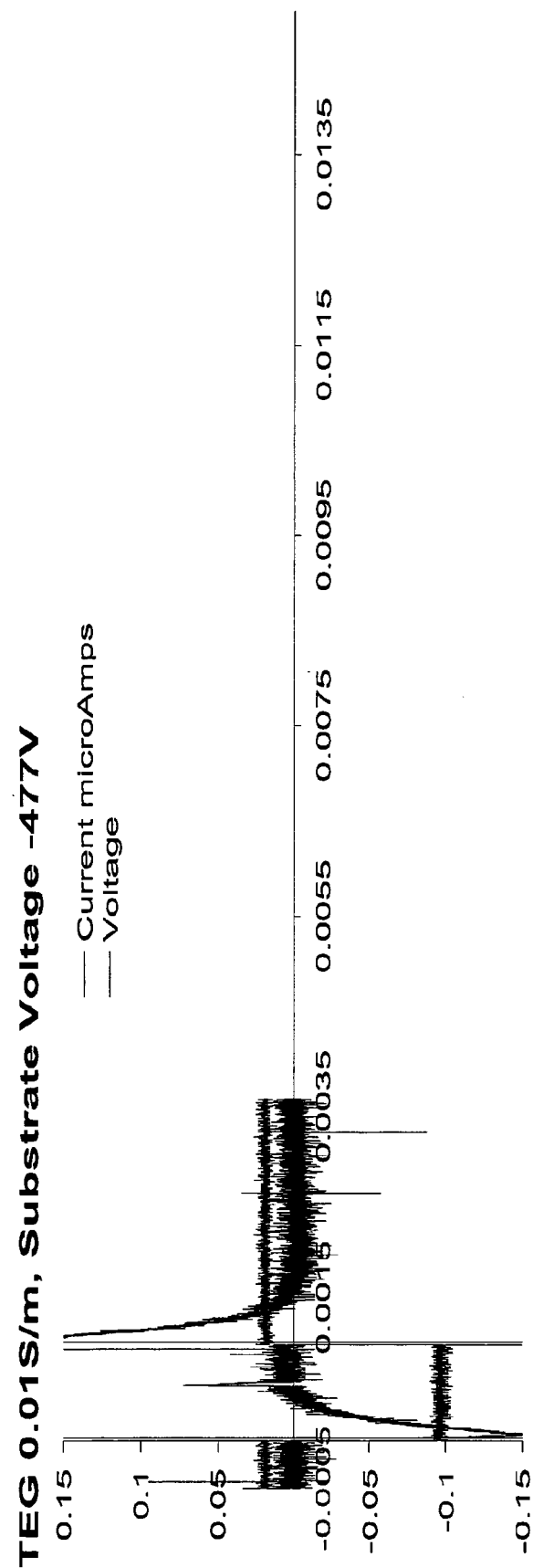
FIGS. 7a, 7b and 7c show graphs of current (indicating pulses of electrospray) against time in a third mode.
Figure 7B:
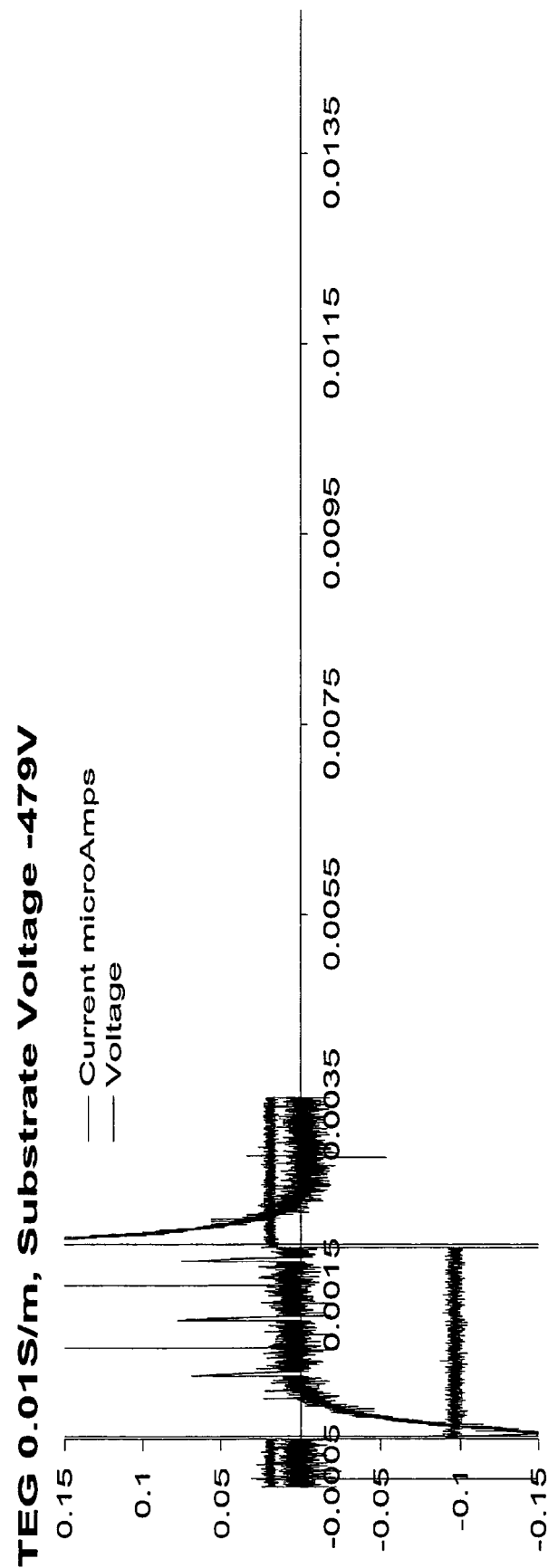
Figure 7C:
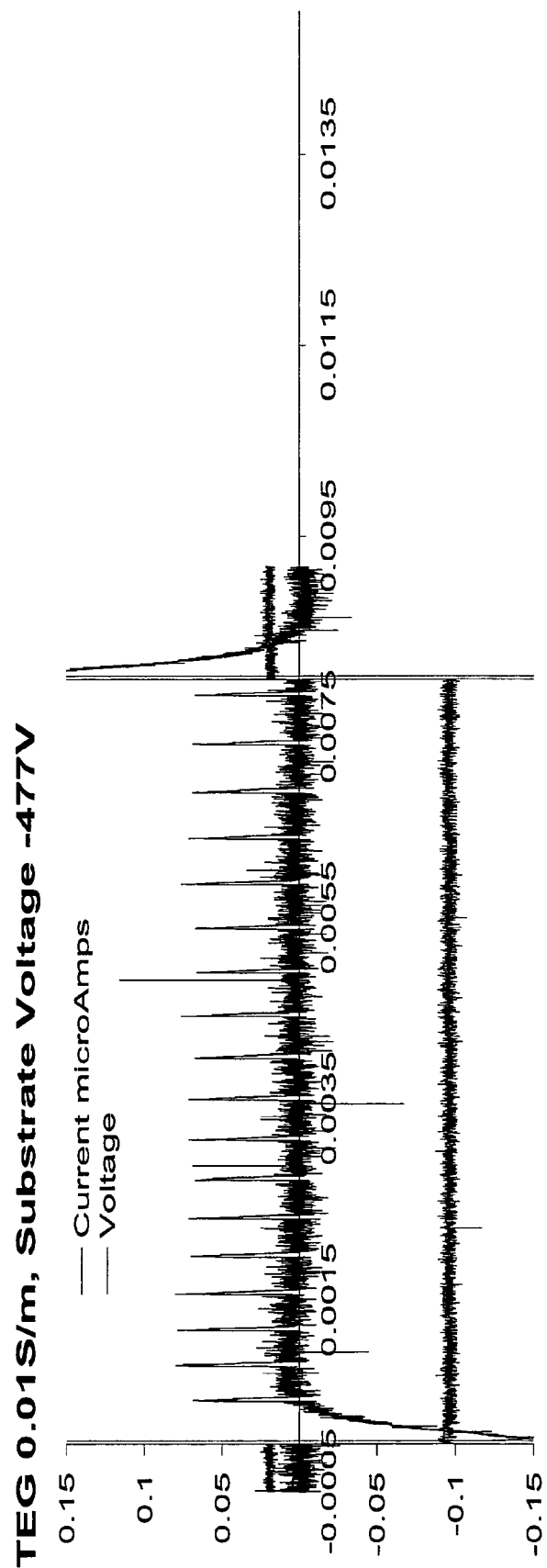

Two main forms of control of the electrospray will now be described (although other forms may be used), being:

1) Varying the voltage or charging current used to control the number of drops emitted in a predetermined time, as will be described as first and second modes and as shown in FIGS. 3a, 3b, 14, 15, 16 and 17; and 2) Varying the time for which the voltage or charging current is applied at a pre-determined voltage or charging current, as will be described as a third mode and as shown in FIGS. 7a to 7c.

The following modes of operation and uses can be used on any of the apparatus described or illustrated herein. The modes of operations and uses may also be used on any apparatus able to emit such pulses of electrospray.

Figure 3A:
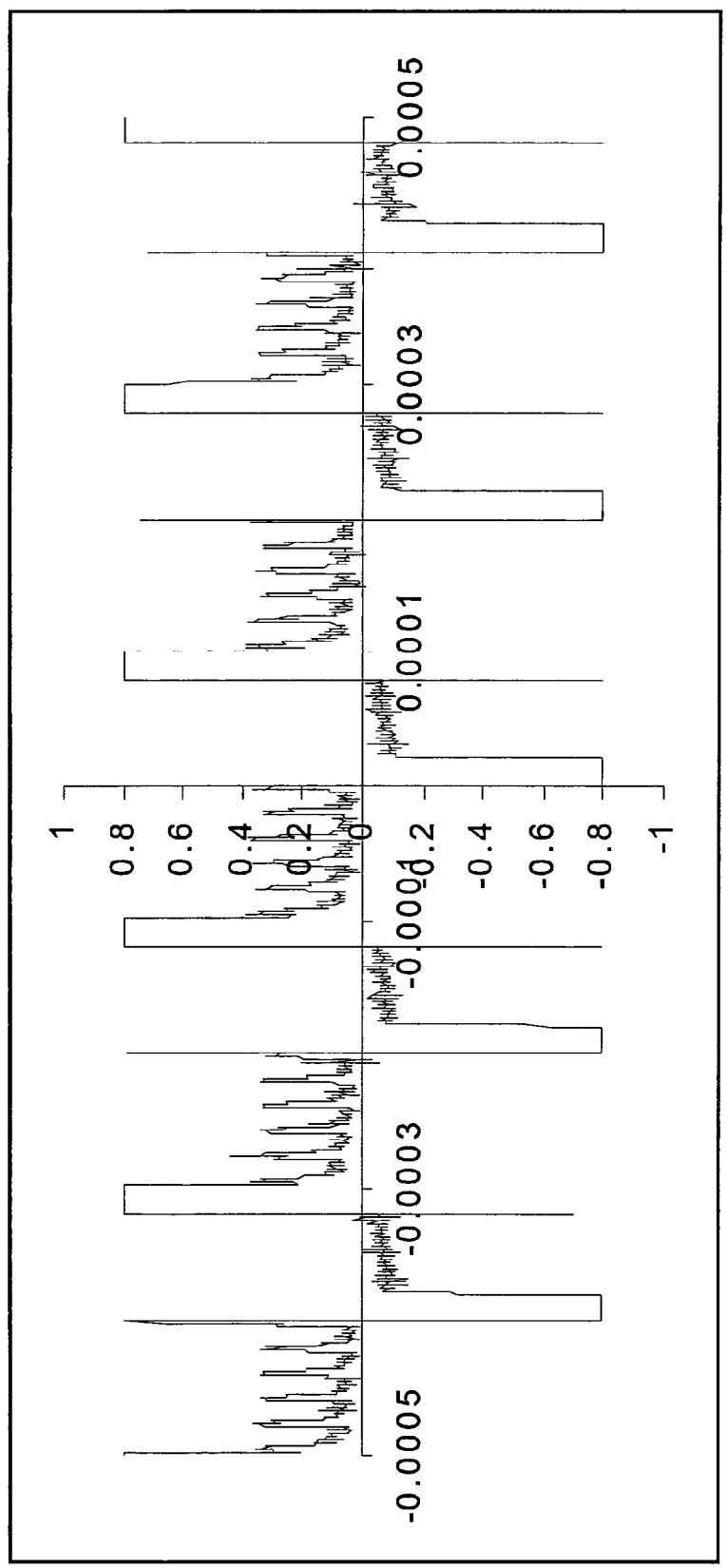
FIGS. 3a and 3b show graphs of current (indicating pulses of electrospray) against time in a first mode.
Figure 3B:
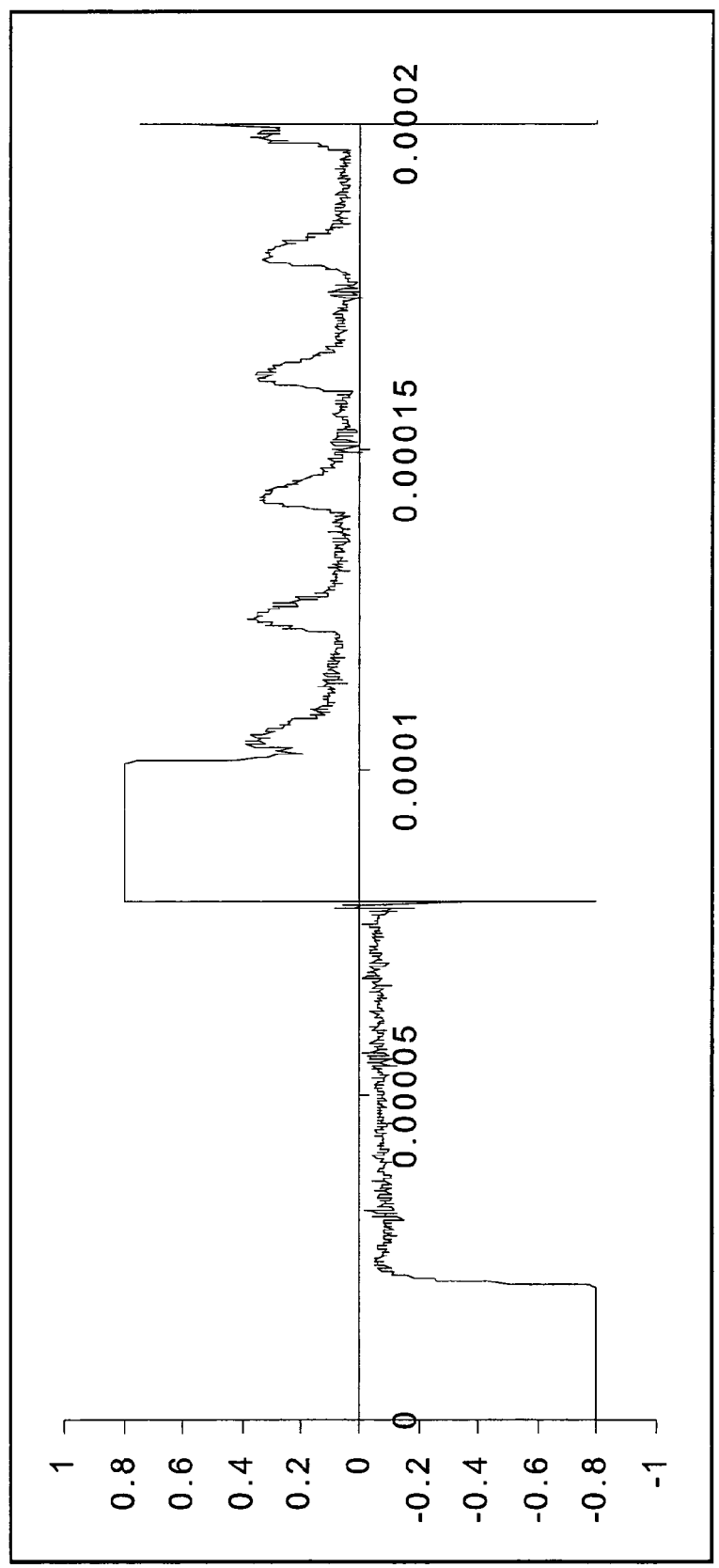

FIGS. 3a and 3b show a first mode of the invention. The liquid to be electrosprayed can be either a conductive or non-conductive liquid, which is the case for all of the described modes. The apparatus used will be based on the appropriate one of FIG. 1 or 1b. The electrospraying apparatus applies a voltage or charging current to the liquid. The voltage applied switches between two voltages or charging currents, preferably repeating the cycle at a rate of 5 kHz. Each of the two voltages may be applied for an equal amount of time, being 0.0001 seconds in that case, or one of the two voltages may be applied for a longer period of time than the other.

A first voltage is applied during a period 110. The first voltage is selected below a minimum threshold for electrospray pulses to be emitted. Therefore, no pulses are emitted during the first period 110. An example voltage is 350V.

In the second period 112, the applied voltage is switched to a higher voltage. The second higher voltage is constant throughout the second period 112 and causes six droplets of electrospray to be emitted from the apparatus at a constant frequency. An example second voltage is 400 V. The voltage then switches back to the first voltage, and the cycle repeats. The voltages or charging currents in the first and second periods are preferably each substantially constant whilst applied to form a square wave, or alternatively may be in the form of a saw tooth or triangular or sinusoidal wave.

FIG. 3b shows an enlarged view of the first period 110 and the second time period 112. The pulses of electrospray are indicated by the peaks 114. Note that the saturated squared off positive and negative currents shown do not represent emitted pulses of electrospray, and are merely caused by the change in applied voltage. The lengths of the periods 110, 112 are different, in particular, the length of the "on/pulse emitting" period 112 is longer than the "off" period 110. Alternatively, the lengths of periods 110,112 may be the same.

Figure 15:
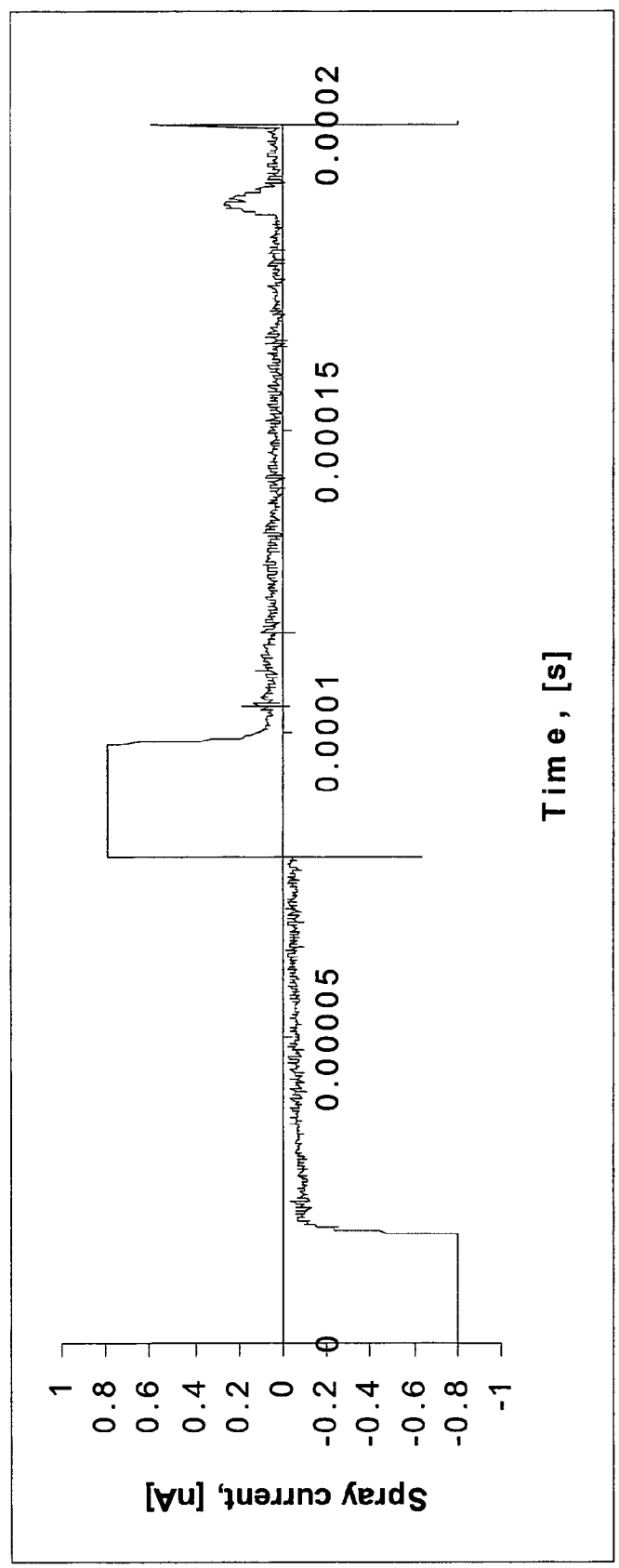
FIG. 15 shows a graph of current (indicating pulses of electrospray) against time in a first mode.

FIG. 15 shows a variation of the first aspect of the invention. The applied voltage cycles at a frequency of 5 kHz between a first voltage and a second voltage. The first voltage is applied during a period 120. The first voltage is selected such that no electrospray pulses are emitted. The second voltage is applied in the second period 122. FIG. 3 shows how selection of voltage will affect the frequency of emitted droplets. The second voltage is selected such that one electrospray pulse 124 is emitted during this time 122. This cycle may then repeat, alternating between the first and second voltages.

Figure 16:
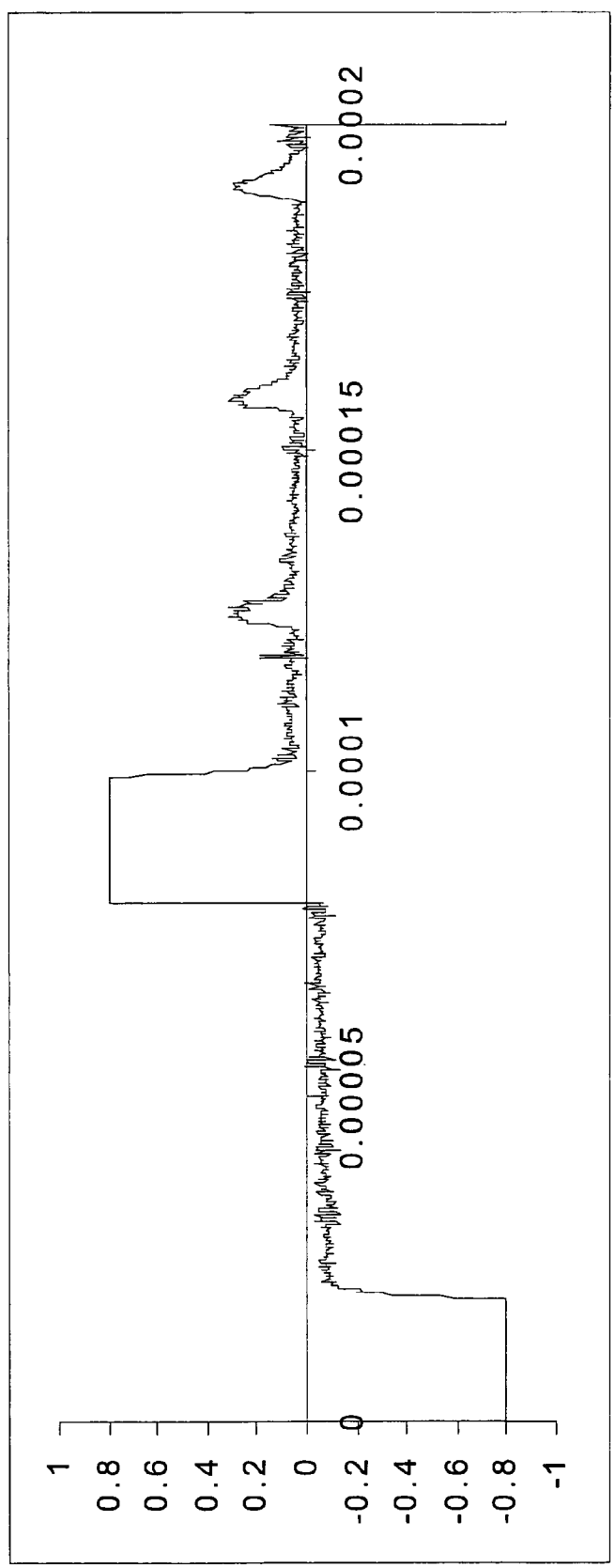
FIG. 16 shows a graph of current (indicating pulses of electrospray) against time in a first mode.

FIG. 16 shows switching between two voltages, as described above. In a first period 130 a first voltage is applied which results in no electrospray droplets being emitted. In a second period 132, a second voltage is applied. The second voltage is selected to cause electrospray to occur at a frequency which results in three electrospray droplets 134 to be emitted during the period 132.

The electric field or charging current is reduced to a non-zero strength when no electrospray is to be emitted. The voltage may be reduced by less than 100V, and preferably between 20 to 50V, when moving from a period in which electrospray is emitted to a period when electrospray is not emitted. Alternatively, the electric field or charging current may be substantially zero when no electrospray is to be emitted.

The time-varying electric field or charging current may be produced in all embodiments by generating a d.c. (or constant) electric field or charging current component. A generally smaller time-varying component is also generated, and superimposed on the constant component.

The time-varying electric field or charging current has been described as a square wave, in which the strength of the electric field or charging current alternates between two values. Both of the alternating values are preferably non-zero, even if no electrospray is emitted in one of them. The waveform of any embodiment may alternately be an irregular, or not be a constant over even part of the waveform. In particular, the waveform may be the form of a sinusoidal-wave, saw tooth or triangular-wave.

Figure 17:
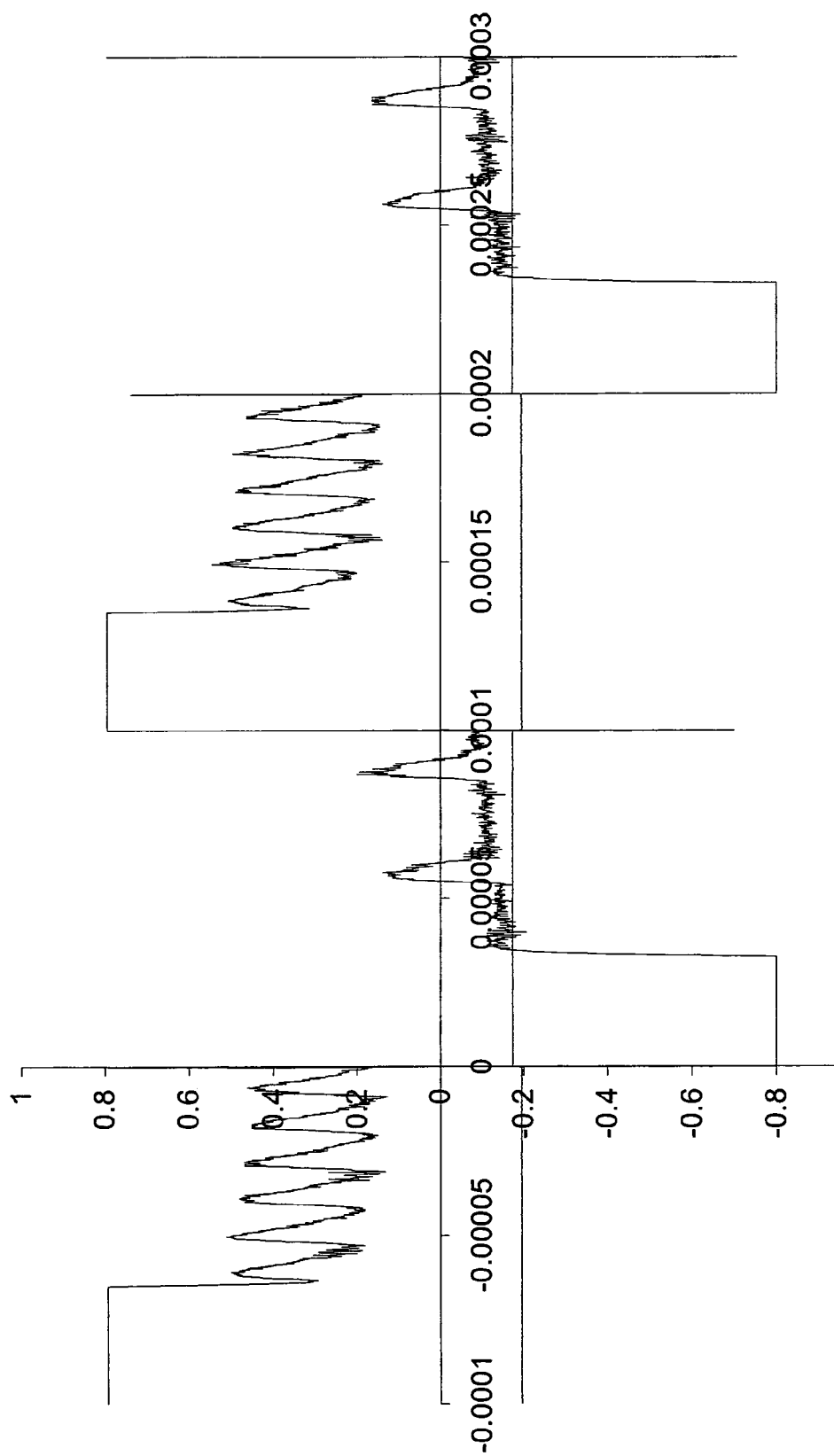
FIG. 17 shows a graph of current (indicating pulses of electrospray) against time in a second mode.

FIG. 17 shows a second aspect of the present invention. During a first time period 140, a constant first voltage is applied to the liquid. The first voltage is selected such that droplets are emitted at a frequency which results in two droplets being emitted in the first time period 140. The apparatus switches to a second voltage, which is applied during a second time period 142. The second voltage is selected to be higher such that six electrospray pulses are emitted during the second time period 142. The apparatus cycles through the first and second voltages at a rate of 5 Khz. The first and second time periods are equal in length, being 0.0001 seconds each. The cycle continues by repeating the first voltage in a third period 148, during which two electrospray pulses are emitted. The rate of emission of pulses, dependent on the voltage or charging current applied, is therefore different in the first and second periods.

The first and second time periods as described above have been shown as being an equal length of time. Alternatively, the first and second time periods may be different lengths of time. The voltage for each time period and the length of time it is applied for can be freely varied to deliver the required volume of liquid at the required rate, or with pre-determined periods of time with no electrospray.

The apparatus may cycle through two, three or more periods of time, each period having a different voltage applied.

FIGS. 7a, 7b and 7c show a third aspect of the invention, which provides an alternative means of control to the first and second aspects. In the third aspect, the on-time of the voltage applied to the liquid can be varied. A constant voltage is applied in order to emit electrospray pulses. The voltage or charging current is applied for a selected length of time to allow the required number of pulses has been emitted. The voltage is then reduced such that further electrospray pulses are not emitted. The voltage can then be switched on again, and the cycle repeated.

The voltage may be reduced just below a minimum threshold value such that no electrospray is emitted, or may be reduced to zero. Preferably, the electric field or charging current is reduced to a non-zero strength when no electrospray is to be emitted. The voltage may be reduced by less than 100V, and preferably between 20 to 50V.

FIG. 7a shows the voltage being switched on for a time period 150. The time period 150 is selected such that there is only time for one pulse 151 to be emitted. The voltage is then reduced for the remainder of the cycle such that no further pulses are emitted.

FIG. 7b shows the voltage switched on for a time period 152. The time period 152 is sufficient to allow three pulses 153 to be emitted.

FIG. 7c shows the voltage being switched on for a time period 154, sufficient for fourteen droplets 155 to be emitted.

The voltage in this aspect is selected depending on the use of the electrospray, in order to give a reasonable rate of spray for that application, which can be accurately controlled.

The apparatus may operate in the third mode in a cycle. The cycle may have a constant period, which may be chosen to be longer than the expected longest length of time for which electrospray is wanted to be emitted. Whilst the electric field or charging current strength is above the threshold strength, electrospray pulses will occur. The length of time for which the electric field or charging current strength is above the threshold strength can be varied. A duty cycle of a waveform can be considered as the proportion of the cycle which the waveform is 'high' or 'on', and so the duty cycle of the waveform will be variable depending on the length of time for which electrospray occur compared to when no electrospray pulses are emitted.

The means for varying the strength of the electric field or charging current in a cycle of constant period may provide a variable duty cycle.

The apparatus may operate in a mode in which the voltage, and length of time that voltage is applied for, can both be varied in order to control the emission of electrospray droplets.

Any of the described features may be combined with any other described feature. Electrospray according to any of the embodiments above has many uses. Some of the possible uses, and how the electrospray is optimised for them, will now be described. These uses and methods of use apply to all embodiments.

Conductive Tracks

Electronic circuits rely on the fabrication of conductive tracks to link components electrically. The present invention may be used as a printer, as an example of a direct writing process. The liquid sprayed may be a suspension of gold nanoparticles, or may be a conductive ink based on silver nitrate. Alternatively, metallo-organic decomposition inks may be used, for example comprising silver neodecanoate dissolved in toluene. The substrate could be silicon, acetate, glass, plastics, papers or other materials. Such conductive inks may have a viscosity of around 10 cP. The present apparatus would preferably use a nozzle diameter of 10 to 50 μm. Other screen printable inks have a viscosity greater than 100 cP, which may be used in the present method with a nozzle diameter of greater than 100 μm.

Plastic Electronics

The use of plastic substrates for electronics allows creation of electronic circuits on a flexible plastic substrate. A plastic substrate presents the problem that it may have a rough surface and a low melting temperature. These problems can be overcome by solution processing, requiring the materials to be printed in solution form onto the plastic at a reasonable temperature. This technology may be able to print the materials desired for this application. Conductive tracks may be printed as described above on the plastic substrate.

Light-Emitting Polymers (e.g. PEDOT—Poly(3,4-Ethylenedioxythiophene)) and Conducting Polymers.

These materials may be mixed in water or a dielectric liquid. The appropriate apparatus described above may be used depending on the conductivity to be electrosprayed, i.e. whether it can be considered conductive or non-conductive. The nozzle diameter can be selected to suit the size of the features required and the solution viscosity. The nozzle diameter may be 5 or 10 μm for small features and a viscosity similar to water.

Display Screens

The apparatus may be used to print Thin Film Transistor (TFT) screens. The substrate used may be glass, and a conductive liquid may be electrosprayed. An integrated electrode may be used, as shown in FIG. 18.

The fabrication of screens may utilise any of the features described for maskless lithography, conductive tracks or plastic electronics.

Tissue Engineering

The apparatus and method can be used for the purpose of tissue engineering, for example by spraying proteins in aqueous solutions. The proteins may range from simple amino acids to large non-covalently bound macromolecules, such as proteosome. The mass of the proteins may extend up to around 1 Mda, and this also allows some viruses to be electrosprayed. Water may be used as the solvent, since it has a suitable viscosity. A wide range of nozzle diameters may be used, and preferably nozzle diameter 10 to 30 μm may be used.

The substrate may be a scaffold made from biodegradable polymers (e.g. PLGA) with a scale of about 10 μm. The apparatus may use an integrated electrode. The protein sprayed may be a functional protein such as fibronectin, albumin or collagen. This would allow cell growth and migration to be controlled on a micro-scale on the scaffold.

The present apparatus may be used to create lipid bi-layers, or scaffolds for proteins. The apparatus may be used for accurate dispensation of liquids, for example, for drug discovery purposes.

Nebulisers

The apparatus may be used in place of a nebuliser, for example to vaporise a liquid medicine or liquid containing a biologically active agent to produce droplets in the preferred region of 0.4 to 6 microns. The vaporised liquid in the form of a mist can then be inhaled by a user.

Transdermal Injection

The apparatus may be used to vaporise a liquid medicine or liquid containing a biologically active agent. This vapour may then be administered topically or transdermally to a user.

Dispensation

The apparatus may be used in combination with a mass spectrometer. The apparatus is suitable for dispensing very small quantities of molecules, e.g. into a mass spectrometer. The substrate may be glass or plastic. The apparatus may be configured to dispense femtolitre volumes to high picoliter volumes of aqueous solutions. The solutions may contain the molecule to be tested.

The present apparatus and method may be used for spraying analytes onto a lab on a chip. The present apparatus may be used for rapid prototyping, or for the production of biological micro arrays. The method can also be used to micropipette solutions, or create micro-arrays.

The apparatus of the present invention may be used for electrospraying proteins or other analytes onto a biosensor.

Maskless Lithography The apparatus of the present invention may be used to transfer a pattern onto a surface. Photolithography uses an etch mask which is often made of a polymer called a photoresist, in which the pattern is created by light exposure.

The present invention can create etch masks either by printing etch resist materials directly onto the surface in the desired pattern, or by printing etchant or resist developer onto the surface to remove either the etch resist or the unwanted useful film from where its is not required.

Printing etch resist materials may use polymers or waxes as the liquids to be electrosprayed. Such liquids are likely to be dielectric (i.e. non-conductive) and so apparatus based on FIG. 1 may be used. A nozzle diameter of greater than 100 µm may be used. The substrate is preferably silicon, or maybe any other material. Etchants or developers are likely to be organic solvents with low viscosities.

Metamaterials

Metamaterials are artificially produced materials with a periodic or cellular structure often called a "super-lattice" or a "photonic crystal". The period of the cells must be comparable to the wavelength of light it interacts with. For visible light, a wavelength of less than one micron would be required. The technique of the present invention may be able to achieve printing on this scale.

Optical Devices

Optical devices can be fabricated from polymers with features on the micron scale. Microfabrication of waveguides and mirror assemblies may be achieved using lithography material deposition and etching processes as discussed above. The liquid to be electrosprayed is preferably a polymer, onto a silicon or glass substrate.

The apparatus of the present invention may be used to fabricate optical devices, such as gratings or holograms. The apparatus for the present invention may be used to manufacture screens comprising organic Light Emitting Diodes (OLEDs) or for a Liquavista® screen.

The apparatus may also be used in the manufacture of sensors, or may be used to print images, using ink or any other liquid as the liquid to be sprayed. The invention may be used in manufacturing, for positioning adhesives, patterning or making electronic components. The electrospray apparatus may be used as a printer, in order to spray inks or print onto chips or substrates.

The uses and applications described are applicable to any apparatus or method utilising inherently pulsed electrospray, and is not limited to the example apparatus or methods of operation described. For example, the uses and applications are applicable when the electric field or charging current strength is reduced to zero (or to a non-zero value) in order to pause electrospray.

The apparatus and method of the present invention may be used to spray a plurality of droplets at one point on a substrate, and then provide relative movement between the substrate and emitter to continue spraying at a different point on the substrate. The relative movement may occur whilst electrospraying is paused by reducing the field strength below a threshold level. The apparatus and method may also be used to spray only one droplet at any point on the substrate, which may be achieved by continuous relative movement of the substrate or emitting only one droplet at a time, and then moving the substrate whilst electrospraying is paused by reducing the field strength below a threshold level.

As will be appreciated by the skilled person, details of the above embodiments may be varied without departing from the scope of the present invention, as defined by the appended claims.

Figure 19:
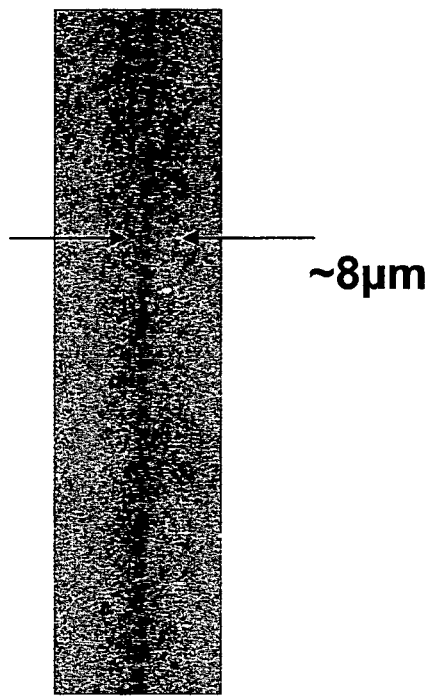
FIG. 19 shows a photograph of drop deposition on a paper substrate.
Figure 20:
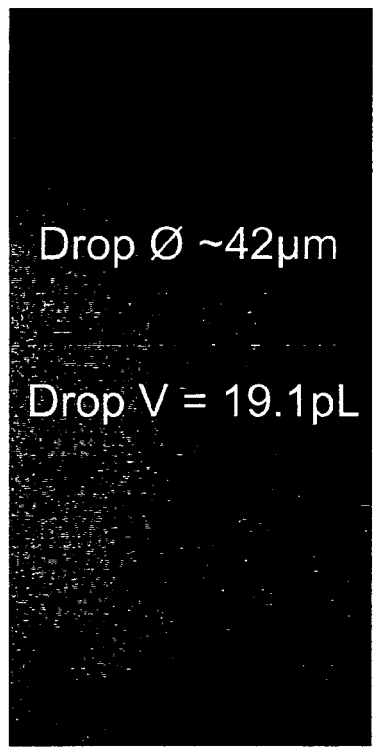
FIG. 20 shows a photograph of drop deposition on an acetate substrate.
Figure 21:
FIG. 21 shows a photograph of drop deposition on a silicon substrate.

For example, the substrate may be paper, silicon, semiconductor, insulator, conductor, card, food, packaging, plastics and skin. FIGS. 19-21 show the results of drop deposition, shown as photographs, on various example substrates. These figures provide an indication of the parameters (voltage, capillary diameter) used to produce various results including drop volume and frequency.

For the embodiment shown in FIG. 8 when a net zero pressure at the emitter is required the liquid free surface within the fluid reservoir 24 may be at the same level as the exit plane of the capillary, for example.

The examples provided above show a substrate moved by a translation stage. Instead, the print head may move and the substrate may be fixed.

At least when non-conductive liquids are used the voltage may be substantially independent of nozzle or emitter exit diameter.

The emission frequency and in particular the maximum emission frequency may be dependent on nozzle or emitter exit diameter. Therefore, varying this diameter may be used to vary this parameter. FIGS. 19-21 provide examples of this dependence.

Many combinations, modifications, or alterations to the features of the above embodiments will be readily apparent to the skilled person and are intended to form part of the invention.

The invention claimed is:

1. An electrostatic spray apparatus for dispensing a controlled volume of substantially non-conductive liquid in pulses onto a substrate, the apparatus comprising:
an emitter having a spray area from which the liquid can be sprayed,
an electrode having an aperture;
a charge injector for being in fluid communication with the liquid and for injecting charges into the liquid, whereby, in use, the liquid is delivered to the spray area by electrostatic forces and electrostatic spraying occurs in uniform pulses through the aperture of the electrode and on to the substrate whilst the charges are injected; and
a controller configured to apply a constant, non-pulsed voltage between the emitter and the electrode, the non-pulsed voltage being operable to provide the uniform pulses of a period independent of the time for which the voltage is applied.

2. An electrostatic spray apparatus as claimed in claim 1 wherein the emitter comprises a cavity for receiving liquid, and the spray area is an aperture in fluid communication with the cavity.

3. A method of electrostatic spraying for dispensing a controlled volume of substantially non-conductive liquid in pulses onto a substrate, the method comprising:
providing an emitter for receiving the substantially non-conductive liquid, the emitter having a spray area from which liquid can be sprayed,
providing an electrode having an aperture;
injecting charges into the liquid by a change injector in fluid communication with the liquid;
whereby the substantially non-conductive liquid is delivered to the spray area by electrostatic forces and electrostatic spraying occurs in uniform pulses through the aperture of the electrode and on to the substrate whilst the charges are injected,
wherein a controller applies a constant, non-pulsed voltage between the emitter and the electrode such that the period of the uniform pulses is independent of the time for which the voltage is applied.

4. A method of electrostatic spraying as claimed in claim 3 wherein the emitter comprises a cavity for receiving liquid, and the spray area is an aperture in fluid communication with the cavity.

5. An electrostatic spray apparatus as claimed in claim 1 wherein the charge injector is a material which can be triboelectrically charged and brought into contact with the emitter.

6. An electrostatic spray apparatus as claimed in claim 1 further comprising a support for holding a substrate in a position spaced from the spray area, such that in use the sprayed liquid is deposited on a surface of the substrate, thereby forming a feature thereon.

7. An electrostatic spray apparatus as claimed in claim 1 wherein the volume of liquid ejected by a single pulse is between 0.1 femtoliter and 1 femtoliter, or between 1 femtoliter and 1 picoliter, or between 1 picoliter and 100 picoliters, or between 100 picoliters and 10 nanoliters, or between 10 nanoliters and 1 microliter.

8. An electrostatic spray apparatus as claimed in claim 1 wherein the apparatus is configured to perform printing.

9. An electrostatic spray apparatus as claimed in claim 1 wherein the apparatus is configured to use a liquid having a conductivity less than $10^{-6}$ s/m.

10. An electrostatic spray apparatus as claimed in claim 1 wherein the spray area is located in a housing, the housing being for containing any gaseous environment including, but not limited to, air, elevated pressure gas, vacuum, carbon dioxide, argon or nitrogen.

11. An electrostatic spray apparatus as claimed in claim 1 comprising a plurality of emitters, each emitter having a means for applying an electric field or charging current to liquid adjacent the spray area.

12. An electrostatic spray apparatus as claimed in claim 11, wherein the means for applying an electric field or charging current is operable to independently control the electric field or charging current at each spray area.

13. An electrostatic spray apparatus as claimed in claim 1 wherein the controller comprises a fast switch for applying an electric field or charging current such that in use, voltage or charging current is turned off or on by the fast switch to precisely control the time for which the electrostatic spray apparatus ejects liquid.

14. A method of electrostatic spraying as claimed in claim 3 wherein a plurality of emitters is provided, and the electric field or charging current applied to each emitter is independently controllable.

* * * * *